US012441739B2

(12) United States Patent
Bai et al.

(10) Patent No.: US 12,441,739 B2
(45) Date of Patent: Oct. 14, 2025

(54) GLUCAGON RECEPTOR ANTAGONIST AND USE THEREOF

(71) Applicants: LANZHOU UNIVERSITY, Lanzhou (CN); TENCENT TECHNOLOGY (SHENZHEN) COMPANY LIMITED, Shenzhen (CN)

(72) Inventors: Qifeng Bai, Shenzhen (CN); Tingyang Xu, Shenzhen (CN); Liya Feng, Shenzhen (CN); Shuo Liu, Shenzhen (CN); Junzhou Huang, Shenzhen (CN); Huanxiang Liu, Shenzhen (CN); Xiaojun Yao, Shenzhen (CN)

(73) Assignees: LANZHOU UNIVERSITY, Lanzhou (CN); TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 498 days.

(21) Appl. No.: 18/074,889

(22) Filed: Dec. 5, 2022

(65) Prior Publication Data

US 2023/0104956 A1 Apr. 6, 2023

Related U.S. Application Data

(63) Continuation of application No. PCT/CN2022/076637, filed on Feb. 17, 2022.

(30) Foreign Application Priority Data

Feb. 20, 2021 (CN) ........................ 202110194113.X

(51) Int. Cl.
*C07D 495/04* (2006.01)
*A61P 3/10* (2006.01)

(52) U.S. Cl.
CPC .............. *C07D 495/04* (2013.01); *A61P 3/10* (2018.01)

(58) Field of Classification Search
CPC .................................................... C07D 495/04
See application file for complete search history.

(56) References Cited

U.S. PATENT DOCUMENTS

| | | | |
|---|---|---|---|
| 2004/0209943 A1 | 10/2004 | Erickson et al. |
| 2009/0325948 A1 | 12/2009 | Hurley et al. |
| 2012/0076753 A1 | 3/2012 | Mandelboim et al. |
| 2013/0280209 A1 | 10/2013 | Mandelboim et al. |

FOREIGN PATENT DOCUMENTS

| | | | |
|---|---|---|---|
| CN | 1774433 A | 5/2006 |
| CN | 101146763 A | 3/2008 |
| CN | 101495186 A | 7/2009 |
| JP | 2009544732 A | 12/2009 |

OTHER PUBLICATIONS

The Japan Patent Office (JPO) Notification of Reasons for Refusal for Application No. 2023-535773 and Translation Jun. 10, 2024 * Pages.

Database Registry [Online] Retrieved from STN and RN 1358514-98-3, printing day Feb. 29, 2012,4,5-Dihydro-7-hydroxy-N-[3-(methylthio) phenyl]-5-oxothieno[3 and 2-b] pyridine-6-carboxamide, Supplier: ChemDiv, Inc.

Database Registry [Online] Retrieved from STN and RN 1358514-65-4, the printing day Feb. 29, 2012, and N-(3-Fluorophenyl)- 4, 5-dihydro-7-hydroxy-5-oxothieno[3 and 2-b] pyridine-6-carboxamide, and Supplier: ChemDiv, Inc.

Database Registry [Online] Retrieved from STN and RN 1358349-48-0, the printing day Feb. 29, 2012, and N-(3-Bromophenyl)-4, 5-dihydro-7-hydroxy-5-oxothieno[3 and 2-b] pyridine-6-carboxamide, and Supplier: ChemDiv, Inc.

Database Registry [Online] Retrieved from STN and RN 1358349-37-7, the printing day Feb. 29, 2012, and N-(4-Ethoxyphenyl)-4, 5-dihydro-7-hydroxy-5-oxothieno[3 and 2-b] pyridine-6-carboxamide, and Supplier: ChemDiv, Inc.

Database Registry [Online] Retrieved from STN and RN 1358349-29-7, the printing day Feb. 29, 2012, N-(3-Chloro-4-methoxyphenyl)-4,5-dihydro-7-hydroxy-5-oxothieno[3,2-b]pyridine-6-carboxa mide, Supplier: ChemDiv, Inc.

Database Registry [Online] Retrieved from STN and RN 1358204-61-1, the printing day Feb. 29, 2012, N-(3-Chlorophenyl)-1,2,5, 6,7,8-hexahydro-4-hydroxy-7-methyl-2-oxo[1]benzothieno[2 and 3-b] pyridine-3-carboxamide, and Supplier: ChemDiv, Inc.

Database Registry [Online] Retrieved from STN and RN 1358202-53-5, the printing day Feb. 29, 2012, and N-(3-Chlorophenyl)-4, 5-dihydro-7-hydroxy-5-oxothieno[3 and 2-b]pyridine-6-carboxamide, and Supplier: ChemDiv, Inc.

Database Registry [Online] Retrieved from STN and RN 1358158-62-9, the printing day Feb. 29, 2012, N-(3-Bromophenyl)-1,2,5, 6,7,8-hexahydro-4-hydroxy-7-methyl-2-oxo[1]benzothieno[2 and 3-b] pyridine-3-carboxamide, and Supplier: ChemDiv, Inc.

(Continued)

*Primary Examiner* — Susanna Moore
(74) *Attorney, Agent, or Firm* — ANOVA LAW GROUP PLLC

(57) ABSTRACT

The present disclosure provides a compound and use thereof as a glucagon receptor antagonist. The compound includes a compound A, or an isomer, metabolite, prodrug, pharmaceutically acceptable ester, or pharmaceutically acceptable salt of the compound A. The glucagon receptor antagonist in the present disclosure has a novel skeleton structure and a low half maximal inhibitory concentration on the glucagon receptor.

(A)

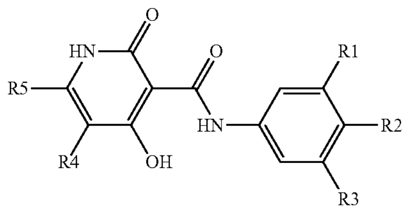

20 Claims, 9 Drawing Sheets

(56) References Cited

OTHER PUBLICATIONS

Database Registry [Online] Retrieved from STN and RN 1358158-13-0, the printing days Feb. 29, 2012, 1, and 2, 5,6,7,8-Hexahydro-4-hydroxy-7-methyl-2-oxo-N-phenyl[1]benzothieno[2,3-b]pyridine-3-carboxamide, Supplier: ChemDiv, Inc.
Database Registry [Online] Retrieved from STN and RN 1358009-36-5, the printing day Feb. 28, 2012, N-(3-Fluorophenyl)-1,2,5,6,7,8-hexahydro-4-hydroxy-7-methyl-2-oxo[1]benzothieno[2 and 3-b]pyridine-3-carboxamide, and Supplier: ChemDiv, Inc.
Database Registry [Online] Retrieved from STN and RN—1359641-55-6, printing day Mar. 2, 2012,4,5-ihydro-7-hydroxy-5-oxo-N-phenylthieno[3 and 2-b] pyridine-6-carboxamide, and Supplier: ChemDiv, Inc.
Database Registry [Online] Retrieved from STN and RN 1359590-64-9, the printing days Mar. 2, 2012, 1,2 and 5,6,7, 8-Hexahydro-4-hydroxy-7-methyl-N-[3-(methylthio) phenyl]-2-oxo[1]benzothieno[2,3-b]pyridine-3-carboxamide, Supplier: ChemDiv, Inc.
Database Registry [Online] Retrieved from STN and RN 1359586-21-2, the printing days Mar. 2, 2012, 1,2 and 5,6,7,8-Hexahydro-4-hydroxy-N-(4-methoxyphenyl)-7-methyl-2-oxo[1]benzothieno[2,3-b]pyridine-3-carboxamide, Supplier: ChemDiv, Inc.
Database Registry [Online] Retrieved from STN and RN 1359578-21-4, the printing day Mar. 2, 2012, N-(3-Chloro-4-methoxyphenyl)-1,2,5,6,7,8-hexahydro-4-hydroxy-7-methyl-2-oxo[1]benzothieno[2 and 3-b]pyridine-3-carboxamide, Supplier: ChemDiv, Inc.
Database Registry [Online] Retrieved from STN and RN 1359507-59-7, the printing day Mar. 2, 2012, N-(4-Ethoxyphenyl)-1,2,5,6,7,8-hexahydro-4-hydroxy-7-methyl-2-oxo[1]benzothieno[2 and 3-b]pyridine-3-carboxamide, and Supplier: ChemDiv, Inc.
Ulla Bjerre Christensen et al. "Linomide increases plasma corticosterone in normal rats, but does not prevent the inhibitory action of IL-1 on β-cells in vivo or ex vivo." Autoimmunity 23.4 (1996): 257-268.
David J Gross et al. "The immunomodulator Linomide: role in treatment and prevention of autoimmune diabetes mellitus." International immunopharmacology 1.6 (2001): 1131-1139.
The European Patent Office (EPO) The Extended European Search Report for 227555612 Mar. 12, 2024 9 Pages.
Database Registry [Online], Chemical Abstracts Service, Feb. 29, 20212, retrieved from STN, Database accession No. 1358158-13-0.
Database Registry [Online], Chemical Abstracts Service, Feb. 29, 20212, retrieved from STN, Database accession No. 1358158-62-9.
Database Registry [Online], Chemical Abstracts Service, Feb. 29, 20212, retrieved from STN, Database accession No. 1358204-61-1.
Database Registry [Online], Chemical Abstracts Service, Mar. 2, 20212, retrieved from STN, Database accession No. 1359507-59-7.
Database Registry [Online], Chemical Abstracts Service, Mar. 2, 20212, retrieved from STN, Database accession No. 1359578-21-4.
Database Registry [Online], Chemical Abstracts Service, Mar. 2, 20212, retrieved from STN, Database accession No. 1359590-64-9.
Database Registry [Online], Chemical Abstracts Service, Mar. 2, 20212, retrieved from STN, Database accession No. 1359586-21-2.
C.G.Wermuth, "The Practice of Medicinal Chemistry (vol. 1)", Tuscan Chemical Co. Ltd., Aug. 15, 1998 (Aug. 15, 1998), (pp. 235-271).
Masakatsu Nozaki et al., "The Practice of Medicinal Chemistry (1st edition)", Chemistry Doujin Co. Ltd. 1995, (pp. 98-99).
The World Intellectual Property Organization (WIPO) International Search Report for PCT/CN2022/076637 May 9, 2022 9 Pages (including translation).
Liangzhen Zheng et al., "OnionNet: a Multiple-Layer Intermolecular-Contact-Based Convolutional Neural Network for Protein-Ligand Binding Affinity Prediction", ACS Omega 2019.
Nicola De cao et al., "MolGAN: An implicit generative model for small molecular graphs", Sep. 27, 2022, arXiv:1805.11973v2.

GLUCAGON RECEPTOR ANTAGONIST AND USE THEREOF

CROSS-REFERENCES TO RELATED APPLICATIONS

This application is a continuation application of PCT Patent Application No. PCT/CN2022/076637, filed on Feb. 17, 2022, which claims priority to Chinese Patent Application No. 202110194113.X, filed on Feb. 20, 2021, the entire contents of both of which are incorporated herein by reference.

FIELD OF THE TECHNOLOGY

The present disclosure relates to the field of medical technologies, and specifically, to a glucagon receptor antagonist and use thereof.

BACKGROUND OF THE DISCLOSURE

Glucagon is a polypeptide hormone secreted by pancreatic islet α cells, consisting of 29 amino acids, mainly acting on the liver. By specifically binding to the glucagon receptor (GCGR) on the surface of liver cells, it can promote hepatic glycogenolysis and gluconeogenesis, causing an increase in blood sugar to counteract the hypoglycemic effect of insulin. The glucagon receptor is a G protein-coupled receptor that exists mainly on the surface of liver cells. It mainly binds to the glucagon to activate adenylate cyclase (AC) and phospholipase C (PLC), causing the concentration of cyclic adenosine monophosphate (cAMP) in the cells to increase, and activating cAMP-dependent protein kinase (PKA).

A glucagon receptor antagonist binds to the glucagon receptor to block the binding of glucagon to the glucagon receptor, inhibiting the function of glucagon, thereby reducing the response activity of cAMP, which is beneficial to lowering blood sugar level and regulating blood sugar balance.

At present, many glucagon receptor antagonists have been reported, but most of them have similar structures. There is a lack of structurally novel compounds as drug candidates. The information disclosed in the above background part is used only for enhancing the understanding of the background of the present disclosure.

SUMMARY

An objective of the present disclosure is to provide a structurally novel glucagon receptor antagonist and use of the glucagon receptor antagonist.

Other features and advantages of the present disclosure will be apparent through the following detailed description, or partly learned through practice of the present disclosure.

According to an aspect of the present disclosure, provided is a first compound, represented by the following structural formula A, or an isomer, metabolite, prodrug, pharmaceutically acceptable ester, or pharmaceutically acceptable salt of the first compound, (A)

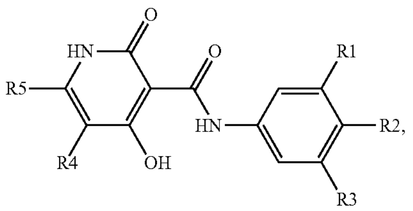

where R1 is H, F, Cl, Br, or I; R2 is H or —O—$(CH_2)_m$—$CH_3$, m being an integer of 0-2; R3 is H or —S—$(CH_2)_n$—$CH_3$, n being an integer of 0-2; and R4 and R5 together form

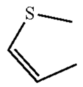

or

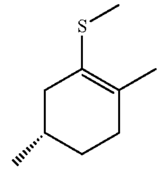

.

According to an aspect of the present disclosure, provided is use of the compound or the pharmaceutical composition in preparing a drug for use as a glucagon receptor antagonist.

According to an aspect of the present disclosure, provided is a compound used as a glucagon receptor antagonist, defined above.

According to an implementation of the present disclosure, the compound is used for treating diseases associated with dysregulation of glucagon metabolism as defined above.

According to an aspect of the present disclosure, provided is a method for treating diseases associated with dysregulation of glucagon metabolism or regulating blood sugar levels, including administering an effective dose of the compound or the pharmaceutical composition to a subject.

According to an aspect of the present disclosure, a glucagon receptor antagonist is provided. The glucagon receptor antagonist includes a compound A or an isomer, acid, ester, metabolite, prodrug, or pharmaceutically acceptable salt of the compound A; and the structural formula of the compound A is:

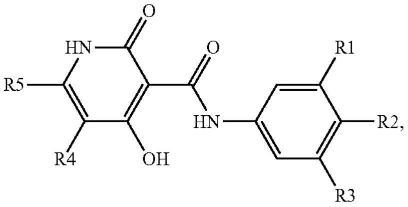

where R1 is independently ‖-H, ‖-F, ‖-Cl, ‖-Br, or ‖-I; R2 is independently ‖-H or ‖-O—$(CH_2)_m$—$CH_3$, m being 0-2; R3 is independently ‖-H or ‖-S—$(CH_2)$n-$CH_3$, n being 0-2; R4 and R5 together form

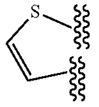

or

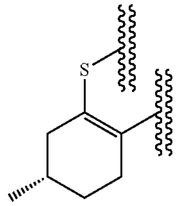

;

and ‖ represents a point of attachment to a parent molecule.

According to an aspect of the present disclosure, a pharmaceutical composition is provided, including a pharmaceutically acceptable carrier and the foregoing glucagon receptor antagonist.

According to an aspect of the present disclosure, a method for regulating a glucagon receptor in a subject is provided, including administering the foregoing glucagon receptor antagonist in a dose that inhibits the glucagon receptor to a subject in need thereof.

According to an aspect of the present disclosure, a method for regulating a glucagon receptor in a subject is provided, including administering the foregoing pharmaceutical composition in a dose that inhibits the glucagon receptor to a subject in need thereof.

According to an aspect of the present disclosure, a method for regulating blood sugar levels in a subject is provided, including administering the foregoing glucagon receptor antagonist in a dose that inhibits the glucagon receptor to a subject in need thereof.

According to an aspect of the present disclosure, a method for regulating blood sugar levels in a subject is provided, including administering the foregoing pharmaceutical composition in a dose that inhibits the glucagon receptor to a subject in need thereof.

According to an aspect of the present disclosure, provided is use of the foregoing glucagon receptor antagonist in preparing drugs for treating diabetes or other diseases associated with dysregulation of glucagon metabolism.

It can be learned from the foregoing technical solutions that the compound that can be used as a glucagon receptor antagonist in the exemplary embodiments of the present disclosure has at least the following advantages and positive effects.

The compound has a novel skeleton structure and a low half maximal inhibitory concentration on the glucagon receptor, and can be used as a promising candidate drug.

It is to be understood in the present disclosure that the above general descriptions and the following detailed descriptions are merely for exemplary and explanatory purposes, and cannot limit the present disclosure.

BRIEF DESCRIPTION OF THE DRAWINGS

The accompanying drawings herein, which are incorporated into the specification and constitute a part of this specification, show embodiments that conform to the present disclosure, and are used for describing a principle of this application together with the present disclosure. Apparently, the accompanying drawings in the following description show only some embodiments of the present disclosure, and a person of ordinary skill in the art may still derive other drawings from these accompanying drawings without creative efforts. In the accompanying drawings.

DESCRIPTION OF EMBODIMENTS

Figure 1:
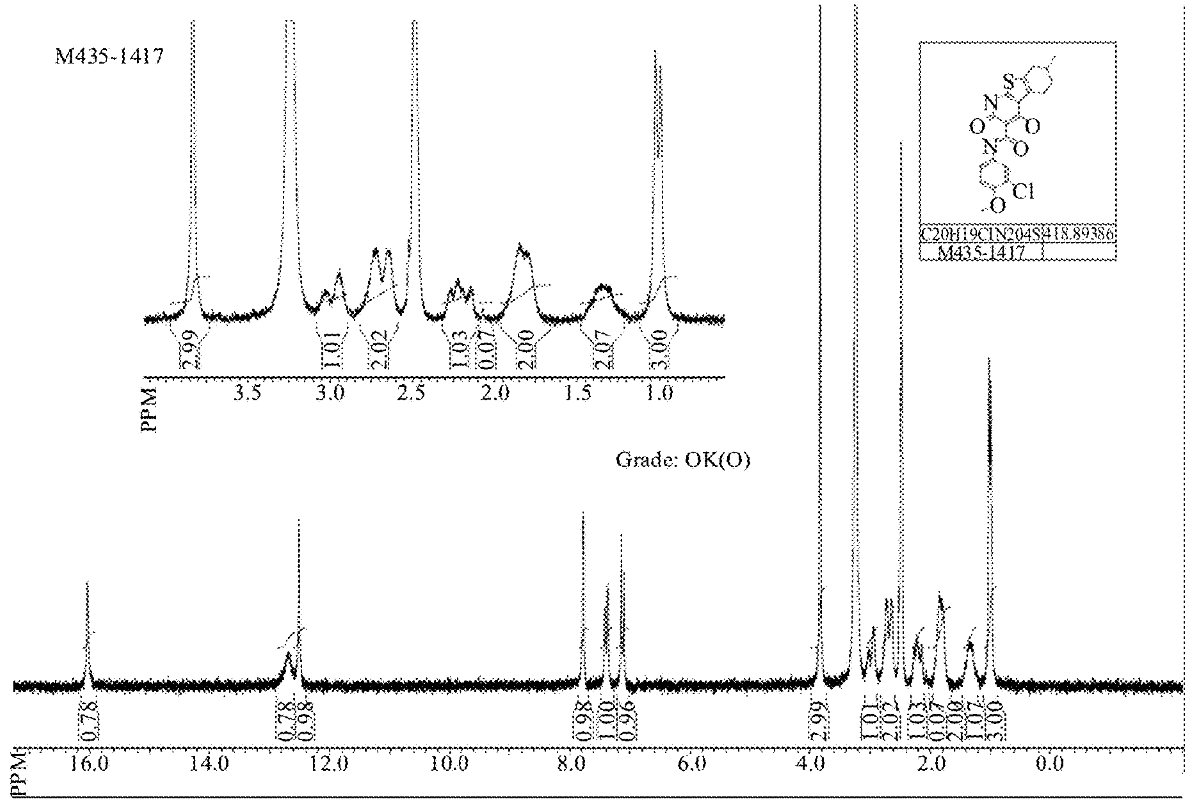
FIG. 1 shows the $^{1}$H-NMR spectrum of a compound A1.

Now, exemplary implementations are described comprehensively with reference to the accompanying drawings. However, the exemplary implementations may be implemented in various forms, and may not be understood as being limited to the examples described herein. Conversely, the implementations are provided to make the present disclosure more comprehensive and complete, and comprehensively convey the idea of the examples of the implementations to a person skilled in the art.

In addition, the described features, structures, or characteristics may be combined in one or more embodiments in any appropriate manner. In the following descriptions, a lot of specific details are provided to give a full understanding of the embodiments of the present disclosure. However, a person skilled in the art is to be aware of that, the technical solutions in the present disclosure may be implemented without one or more of the particular details, or other methods, unit, apparatus, or step may be adopted. In other cases, well-known methods, apparatuses, implementations, or operations are not shown or described in detail, to avoid obscuring the aspects of the present disclosure.

The flowcharts shown in the accompanying drawings are merely examples for descriptions, do not necessarily include all content and operations/steps, and are not necessarily performed in the described order. For example, some operations/steps may be further divided, while some operations/steps may be combined or partially combined. Therefore, an actual execution order may vary depending on an actual situation.

Glucagon and insulin are two hormones, with completely opposite effects, secreted by pancreatic islet cells. Glucagon is secreted by pancreatic islet a cells, and insulin is secreted by pancreatic islet β cells. These two hormones interact and restrict each other to maintain blood glucose homeostasis. Glucagon acts to increase blood sugar. For example, excessive secretion of insulin leads to less secretion of glucagon, so that blood sugar decreases; conversely, excessive secretion of glucagon leads to less secretion of insulin, so that blood sugar increases.

Glucagon works with insulin to maintain normal blood sugar levels. Disturbing the balance of glucagon and insulin levels can cause various diseases, such as diabetes and ketoacidosis.

After glucagon binds to the glucagon receptor, it converts the signal into the cell, and activates the phosphorylase of hepatocytes through the cAMP-PK system to accelerate glycogenolysis. Therefore, reducing the expression of the glucagon receptor can regulate blood sugar levels.

The glucagon receptor antagonist provided in the embodiments of the present disclosure specifically binds to the glucagon receptor to block the binding of the glucagon receptor to glucagon, so as to regulate blood sugar balance.

For this reason, the present disclosure provides a compound that can be used as the glucagon receptor antagonist.

The compound used as the glucagon receptor antagonist may be selected from the group consisting of a compound A with the following structural formula, an isomer, metabolite, prodrug, pharmaceutically acceptable ester, or pharmaceutically acceptable salt of the compound A. Specifically, the structural formula of the compound A is:

(A)

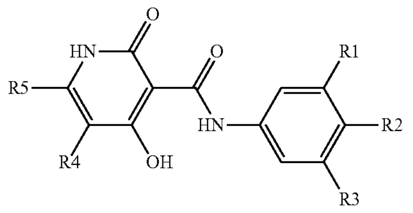

where,

R1 may be H, F, Cl, Br, or I. When R1 is H, there is no substitution at R1 on the benzene ring of the structural formula. When R1 is F, Cl, Br, or I, there is a substitution at R1 on the benzene ring of the structural formula. In some embodiments of the present disclosure, R1 is Cl or H.

R2 is H or $—O—(CH_2)_m—CH_3$, m being an integer of 0-2. When R2 is H, there is no substitution at R2 on the benzene ring of the structural formula.

When m is 0, R2 is $—O—CH_3$. When m is 1, R2 is $—O—CH_2—CH_3$. When m is 2, R2 is $—O—(CH_2)_2—CH_3$. In some embodiments of the present disclosure, R2 is H or $—O—CH_3$.

R3 is —H or $—S—(CH_2)_n—CH_3$, n being an integer of 0-2. When R3 is H, there is no substitution at R3 on the benzene ring of the structural formula.

When m is 0, R3 is $—S—CH_3$. When m is 1, R3 is $—S—CH_2—CH_3$. When m is 2, R3 is $—S—(CH_2)_2—CH_3$. In some embodiments of the present disclosure, R3 is H or $—S—CH_3$.

R4 and R5 together form

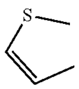

or

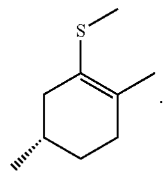

.

The isomer of the compound A includes an optical isomer and a geometric isomer.

The optical isomer is specifically, when R4 and R5 together form the chiral substituent

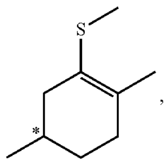

, not limited to

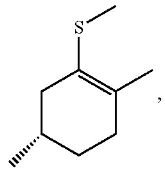

, and may alternatively be

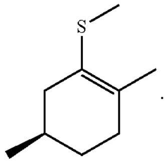

.

The geometric isomer refers to a cis-trans isomer in the present disclosure. Specifically, the geometric isomer in the present disclosure is formed by different arrangements of the double bonds of the parent molecule or the groups at the ring carbon atoms, and by different arrangements of the double bonds in the substituents of R4 and R5 or the groups at the ring carbon atoms.

The ester of the compound A may be obtained by reacting the compound A with organic acids. The ester has the functional group —COO—, and is obtained by dehydration condensation. For example, the organic acid reacts with —OH in the compound A to obtain the ester. The organic acid may be formic acid, acetic acid, propionic acid, or the like. The metabolite of the compound A refers to a product from which some functional groups are metabolized on the compound A. The metabolite refers to a substance produced or consumed by metabolism, and does not substantially affect the medicinal properties of the compound A.

The prodrug of the compound A, also referred to as pro-drug, a drug precursor, a precursor drug, and the like, refers to a compound which is obtained after chemical structure modification on the compound A, is inactive or less active in vitro, and releases the active drug through enzymatic or non-enzymatic conversion in vivo to achieve drug effects. That is, the prodrug of the compound A is generally a functional derivative of the compound A, which is readily converted to the compound A in vivo.

A solvate of the compound A refers to a form in which the compound A is diluted in a certain solvent. Common solvents include water, ethanol, dimethyl sulfoxide, and other liquid substances that can dissolve the compound A.

The pharmaceutically acceptable salt of the compound A includes salts formed in the following two ways.

(1) A salt is formed by the acidic functional group (such as —OH) in the compound A in the present disclosure with proper inorganic or organic cations (bases), such as a salt of the compound A in the present disclosure with an alkali metal or an alkaline earth metal, an ammonium salt of the compound A in the present disclosure, and a salt of the compound A in the present disclosure with a nitrogen-containing organic base. (2) A salt is formed by the basic functional group (such as —NH—) in the compound A in the present disclosure with proper inorganic or organic anions (acids), such as a salt of the compound in the present disclosure with an inorganic acid or an organic carboxylic acid.

Therefore, the pharmaceutically acceptable salt of the compound A in the present disclosure includes, but is not limited to, an alkali metal salt such as a sodium salt, a potassium salt, and a lithium salt; an alkaline earth metal salt such as a calcium salt and a magnesium salt; another metal salt such as an aluminum salt, an iron salt, a zinc salt, a copper salt, a nickel salt, and a cobalt salt; an inorganic alkali salt such as an ammonium salt; an organic alkali salt such as a tert-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylamine salt, and a tris(hydroxymethyl)aminomethane salt; an inorganic acid salt, for example, a hydrohalic acid salt, such as a hydrofluoric acid salt, a hydrochloride salt, a hydrobromide salt, a hydroiodic acid salt, further, a nitrate, a perchlorate, a sulfate, and a phosphate; a lower alkane sulfonate salt such as a mesylate, a triflate, and an ethanesulfonate; an aryl sulfonate such as a benzenesulfonate and a p-benzenesulfonate; an organic carboxylate such as an acetate, a malate, a fumarate, a succinate, a citrate, a tartrate, an oxalate, and a maleate; and an amino acid salt such as a glycinate, a trimethylglycinate, an arginine salt, an omithine salt, a glutamate, and an aspartate salt.

In an exemplary embodiment, R1 is —Cl, R2 is —O—$CH_3$, R3 is —H, and R4 and R5 together form

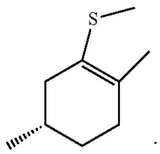

.

In this case, the compound A is:

(A1)

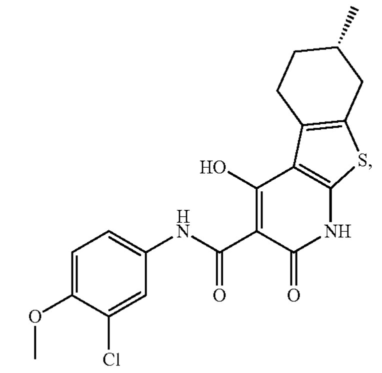

denoted as compound A1.

The compound A1 has a molecular formula of $C_{20}H_{19}ClN_2O_4S$, with the name of (7S)—N-(3-chloro-4-methoxyphenyl)-4-hydroxy-7-methyl-2-oxo-5,6,7,8-tetrahydro-1H-[1]benzothiolo[2,3-b]pyridine-3-carboxamide.

InChI=1S/C20H19ClN2O4S/c1-9-3-5-11-14(7-9)28-20-15(11)17(24)16(19(26)23-20)18(25)22-10-4-6-13(27-2)12(21)8-10/h4,6,8-9H,3,5,7H2,1-2H3,(H,22,25)(H2,23,24,26)/t9-/m0/s1.

The SMILES sequence is: COc1ccc(NC(=O)c2c(O)c3c4c(sc3[nH]c2=0)C[C@@H](C)CC4)cc1Cl.

The compound A1 may be prepared by any known method. Commercially available compound A1 is used in the following embodiments.

FIG. 1 shows the $^{1}H$ NMR spectrum of the compound A1. The solvent is dimethyl sulfoxide (DMSO). This figure indicates that the molecular structure of the compound A1 is determined as the structure represented by the formula A1.

Figure 2:
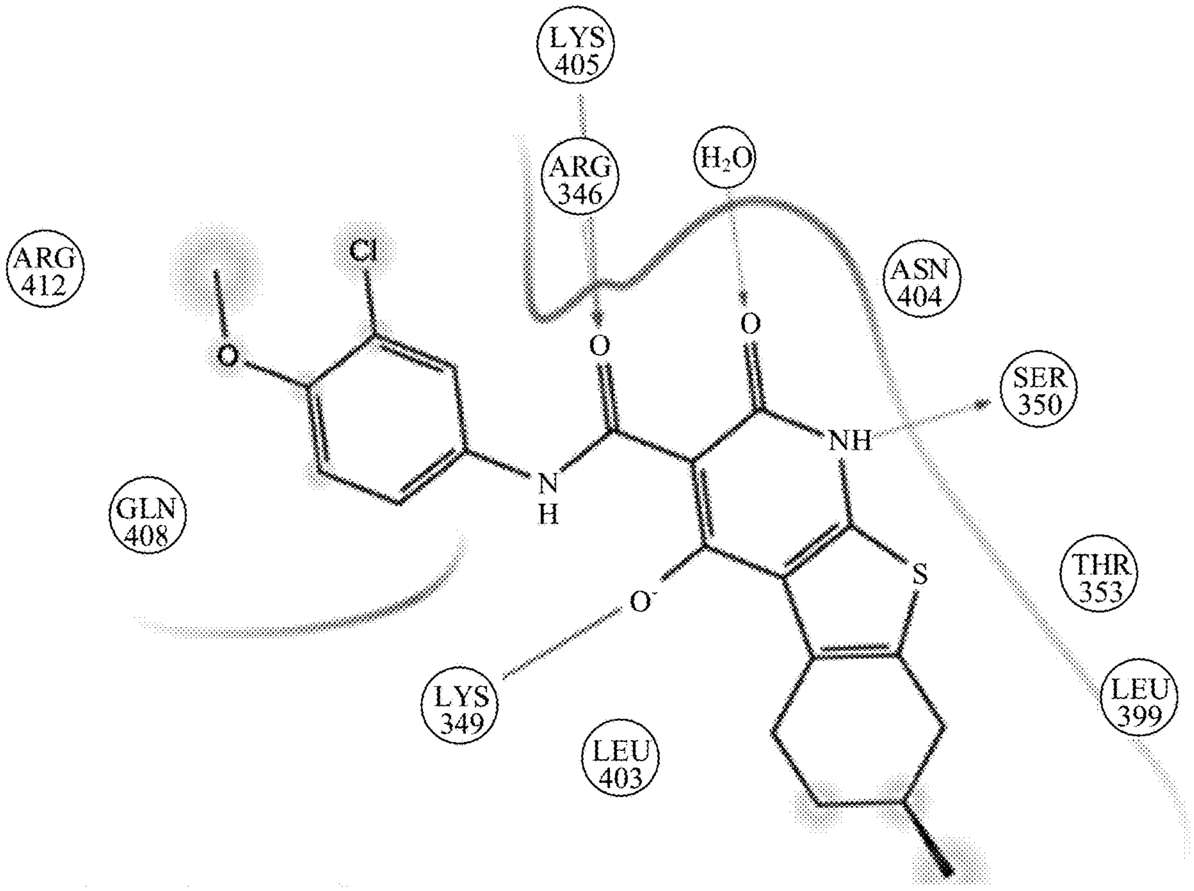
FIG. 2 is a schematic 2D diagram of the interaction between the compound A1 and a glucagon receptor.

FIG. 2 is a schematic 2D diagram of the interaction between the compound A1 and a glucagon receptor. In this figure, ARG412, LYS405, ARG346, ASN404, SER350, THR353, LEU399, LEU403, LYS349, and GLN408 are amino acid residues in the amino acid sequence of the glucagon receptor. In the sequence of proteins, the amino and carboxyl groups between amino acids are dehydrated to form bonds. Some groups of the amino acid are involved in the formation of peptide bonds, so the remaining structural parts are referred to as amino acid residues.

LYS405, ARG346, SER350, and LYS349 all interact with the compound A1. When interacting, LYS405 and ARG346 are hydrogen donors and form hydrogen bonding interactions with the O atom on the compound A1. SER350 is a hydrogen acceptor and forms hydrogen bonding interactions with the H atom on the compound A1. LYS349 and $O^-$ in the compound A1 are attracted to each other through a salt bridge, that is, an ionic bond. Therefore, the above amino acid residues are all capable of interacting with the compound A1.

In addition, the mutation experiment reported in the relevant literature (Jazayeri A, Andrew S. Doré, Lamb D, et al. Extra-helical binding site of a glucagon receptor antagonist [J] Nature, 2016, May 12; 533(7602): 274-277) confirmed that LYS405, ARG346, SER350, and LYS349 are key residues in the binding pocket. The compound A1 in this embodiment can interact with the above residues, so the compound A1 well binds to the binding pocket.

In another exemplary embodiment, R1 is —H, R2 is —H, R3 is —S—$CH_3$, and R4 and R5 together form

In this case, the compound A is:

(A2)

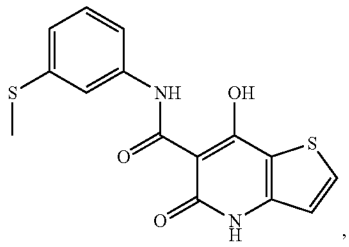

denoted as compound A2.

The compound A2 has a molecular formula of $C_{15}H_{12}N_2O_3S_2$, with the name of 3-(azepan-1-ylcarbonyl)-N-(2,5-difluoro-phenyl)-7-methyl-1,8-naphthyridin-4-amine.

InChI=1S/C15H12N2O3S2/c1-21-9-4-2-3-8(7-9)16-14(19)11-12(18)13-10(5-6-22-13)17-15(11)20/h2-7H,1H3,(H,16,19)(H2,17,18,20).

The SMILES sequence is: CSc1cccc(NC(=O)c2c(O)c3sccc3[nH]c2=O)c1.

The compound A2 may be prepared by any known method. Commercially available compound A2 is used in the following embodiments.

Figure 3:
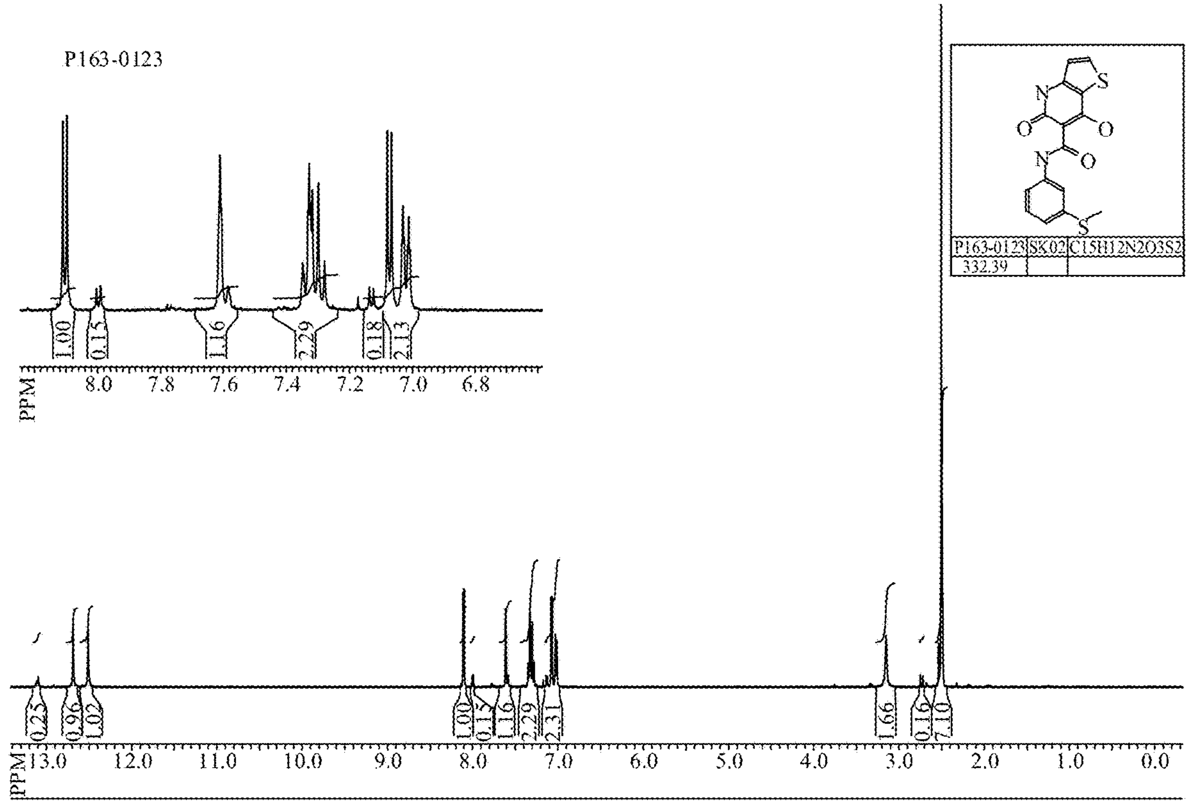
FIG. 3 shows the $^{1}$H-NMR spectrum of a compound A2.

FIG. 3 shows the $^1$H NMR spectrum of the compound A2. The solvent is dimethyl sulfoxide (DMSO). This figure indicates that the molecular structure of the compound A2 is determined as the formula A2.

Figure 4:
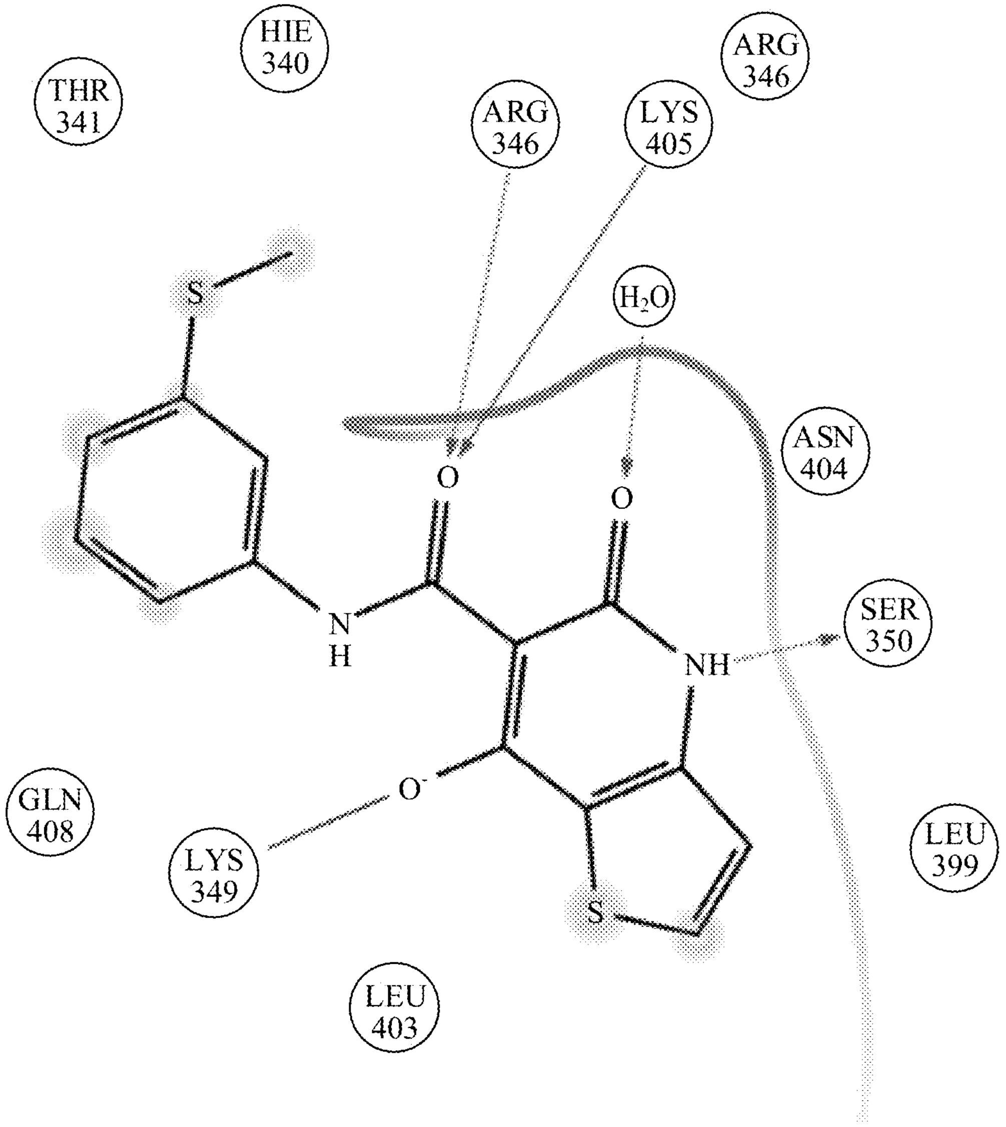
FIG. 4 is a schematic 2D diagram of the interaction between the compound A2 in FIG. 3 and a glucagon receptor.

FIG. 4 is a schematic 2D diagram of the interaction between the compound A2 and a glucagon receptor. In this figure, THR341, HIE340, ARG346, LYS405, ASN404, SER350, LEU399, GLN408, LYS349, and LEU403 are amino acid residues in the amino acid sequence of the glucagon receptor. ARG346, LYS405, SER350, and LYS349 all interact with the compound A2.

LYS405 and ARG346 are hydrogen donors and form hydrogen bonding interactions with the O atom on the compound A2. SER350 is a hydrogen acceptor and forms hydrogen bonding interactions with the H atom on the compound A2. LYS349 and $O^-$ in the compound A2 are attracted to each other through a salt bridge, that is, an ionic bond. Therefore, the above amino acid residues are all capable of interacting with the compound A2.

The compound A2 in this embodiment can interact with the above residues, so the compound A2 well binds to the binding pocket.

In order to determine the antagonistic activity of the compound A on the glucagon receptor in the above embodiments, a cell viability test is carried out. The specific implementation is as follows.

A known human glucagon receptor (hGCGR) antagonist drug is selected as a positive control, and the compound A in the above embodiments, a glucagon peptide segment (that is, human full-length glucagon), and human embryonic kidney cells containing target receptor molecules are mixed. The glucagon peptide segment binds to hGCGR to activate the hGCGR signaling pathway and release the second messenger cAMP. The compound A acts as an antagonist to inhibit the activity of hGCGR.

In an exemplary embodiment, a known hGCGR antagonist drug (L-168,049) is selected as a positive control. L-168,049 has the name of 4-[3-(5-bromo-2-propoxyphenyl)-5-(4-chlorophenyl)-1H-pyrrol-2-yl]pyridine, and is a noncompetitive glucagon receptor antagonist. In addition, in view of the human glucagon receptor on the cell membrane of human embryonic kidney cells HEK293, HEK293 is used to test the drug activity of the human glucagon antagonist. In this embodiment, different concentrations of compound A of the present disclosure and the positive control are respectively mixed with glucagon peptide segments and HEK293 cells, the second messenger cAMP is detected through homogeneous time resolved fluorescence (HTRF), and a half maximal inhibitory concentration value of each compound is calculated according to the intensity value of HTRF.

In an exemplary embodiment, the activity of the compound A is tested using the HTRF technique. Specifically, after activation of the glucagon receptor by the glucagon peptide segment, the second messenger cAMP is released from the glucagon receptor cells, the second messenger cAMP may be detected by HTRF, and the half maximal inhibitory concentration (IC50) of the tested compound may be calculated according to the fluorescence intensity.

In an exemplary embodiment, 11 identical concentration gradients are set for the compounds A1 and A2 respectively. The activities of the compounds A1 and A2 are determined by the HTRF second messenger cAMP response experiment in triplicate. The experimental data obtained is shown in Table 1.

TABLE 1

| Concentration | Compound A1 | | | Compound A2 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 98.36784 | 95.2799 | 96.14817 | 103.2945 | 102.1097 | 103.2736 | 100.4281 |
| −5.477121 | 87.84198 | 83.27731 | 83.50867 | 106.1285 | 105.9119 | 107.3553 | 98.6132 |
| −5.954243 | 75.44346 | 83.23603 | 79.30265 | 84.31701 | 92.47757 | 91.04928 | 98.05019 |
| −6.431364 | 54.65901 | 24.56393 | 41.98704 | 40.16475 | 62.73851 | 47.64906 | 93.04975 |
| −6.908485 | −13.6386 | 2.206529 | −0.67812 | 42.6475 | 14.48349 | 29.53025 | 89.45811 |
| −7.385606 | 35.8205 | 18.90853 | 45.6947 | 5.293268 | 31.48621 | 31.78721 | 47.8261 |
| −7.862728 | 7.61974 | −2.13549 | −0.78096 | −24.902 | 51.04536 | 18.00119 | 28.98286 |
| −8.339849 | 30.02611 | 27.22016 | 3.938939 | 33.24314 | −0.7378 | 10.67377 | 3.941144 |

TABLE 1-continued

| Concentration | Compound A1 | | | Compound A2 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −8.81697 | −22.4972 | 19.34481 | 15.31759 | −19.9622 | 10.71795 | 11.92987 | −8.05055 |
| −9.294091 | 4.979932 | −28.5437 | 23.09991 | 15.16754 | 29.87882 | 11.08606 | −3.76273 |
| −9.771213 | 3.18964 | −35.8803 | −3.23056 | −4.69973 | 3.389463 | −14.8291 | −1.911 |

Figure 5:
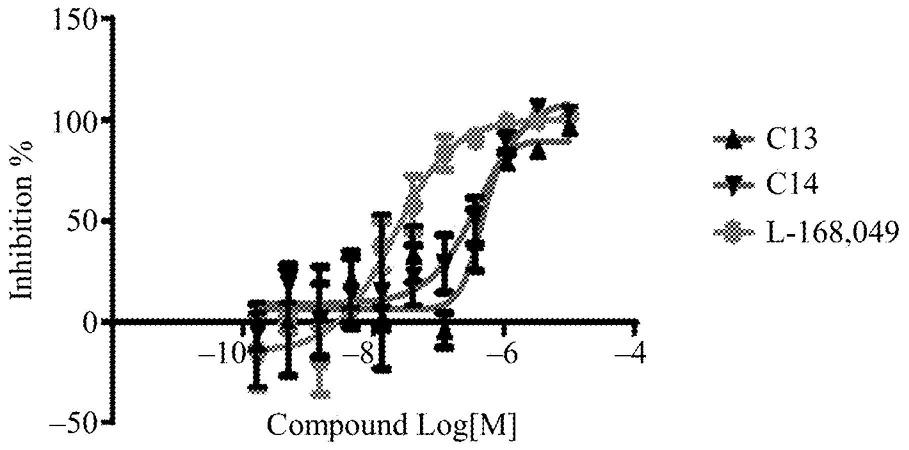
FIG. 5 is a curve graph showing the experimental results of the response of the compound A1 and the compound A2 to cAMP.

The data in Table 1 is processed through software using the concentration gradient as the abscissa and the inhibition percentage as the ordinate, to obtain FIG. 5. FIG. 5 is a curve graph showing the experimental results of the response of the tested compound to cAMP. Specifically, this figure shows the inhibition percentages of the responses of L-168, 049, compound A1, and compound A2 respectively. L-168, 049 is a positive control drug, the compound A1 is represented by C13, and the compound A2 is represented by C14. It can be seen from the figure that both compound A1 and compound A2 have good inhibitory activity of glucagon receptor.

Specifically, the test results are that IC50 of L-168,049 is 2.082E-08 M, IC50 of compound A1 is 4.465E-07 M, and IC50 of compound A2 is 4.225E-07 M.

The values of half maximal inhibitory concentration IC50 of compound A1 and compound A2 are small, which are 446.5 nM and 422.5 nM respectively, so they can be used as structurally novel glucagon receptor antagonist candidate drugs.

An embodiment of the present disclosure also provides use of the compound A in preparing drugs for treating diabetes or other diseases associated with dysregulation of glucagon metabolism.

The diseases associated with dysregulation of glucagon metabolism include, but are not limited to, diabetes (type I diabetes or type II diabetes), hyperglycemia, hyperinsulinemia, β-cell rest, abnormal β-cell function (that is, the compound can improve β-cell function by restoring the initial response), dietary hyperglycemia, apoptosis (that is, the compound can prevent apoptosis), impaired fasting glucose (IFG), metabolic syndrome, hypoglycemia, hyper/hypokalemia, disorder of glucagon levels (that is, the compound can normalize glucagon levels), dysregulation of the LDL/HDL ratio (that is, the compound can improve the LDL/HDL ratio), less snacks, eating disorder, weight loss, polycystic ovary syndrome (PCOS), obesity caused by diabetes, latent autoimmune diabetes (potentially admitted autoimmune diabetes), insulitis, islet transplantation, childhood diabetes, gestational diabetes, late complications of diabetes, micro/macro proteinuria, kidney disease, retinopathy, neuropathy, diabetic foot ulcers, decreased bowel motility due to glucagon administration, broken bowel syndrome, anti-diarrhea, increased gastric secretion, decreased blood flow, erectile dysfunction, glaucoma, post-operative stress, organ tissue damage caused by blood reperfusion after ischemia (that is, the compound can ameliorate organ tissue damage caused by blood reperfusion after ischemia), ischemic heart injury, insufficiency of heart function, congestive heart failure, stroke, myocardial infarction, arrhythmia, premature infant death, anti-apoptotic, wound healing, impaired glucose tolerance (IGT), insulin resistance syndrome, syndrome X, hyperlipidemia, dyslipidemia, hypertriglyceridemia, hyperlipoproteinemia, hypercholesterolemia, arteriosclerosis, and the like.

An embodiment of the present disclosure further provides a pharmaceutical composition including the foregoing glucagon receptor antagonist and a pharmaceutically acceptable carrier.

In this specification, the pharmaceutically acceptable carrier refers to a substance that is compatible with an individual recipient and suitable for delivering an active agent to a target without affecting the activity of the agent.

The pharmaceutical composition is suitable for use in mammals, further, in human. Unless otherwise specified, the following administration subjects are the same as those described herein.

The pharmaceutically acceptable carrier includes any and all solvents, diluents and other liquid vehicles, dispersion or suspension aids, surfactants, pH adjusting agents, isotonicity agents, thickening or emulsifying agents, preservatives, solid binders, lubricants, and the like, as appropriate for the particular dosage form desired.

Various carriers and known preparation techniques for formulating pharmaceutically acceptable compositions are disclosed by Remington: The Science and Practice of Pharmacy, 20th Edition, A. Gennaro, Lippincott Williams & Wilkins in 2000. Pharmaceutically acceptable excipients used in commercial products to dissolve compounds for oral or parenteral administration are reviewed by Strickley, Pharmaceutical Research, 21(2)201-230(2004). Unless a carrier medium is incompatible with the glucagon receptor antagonist of the present disclosure, such as producing any undue biological effect or otherwise interacting in a detrimental manner with any other component of the pharmaceutically acceptable composition, its use is encompassed within the scope of the present disclosure.

The pharmaceutically acceptable carrier includes (but is not limited to) an ion exchanger, aluminum oxide, aluminum stearate, lecithin, serum protein (such as human serum albumin), buffer (such as phosphate, carbonate, magnesium hydroxide, and aluminum hydroxide), glycine, sorbic acid or potassium sorbate, a mixture of partial glycerides of saturated vegetable fatty acids, water, pyrogen-free water, a salt or electrolyte (such as protamine sulfate, disodium hydrogen phosphate, potassium hydrogen phosphate, sodium chloride, and zinc salt), colloidal silica, magnesium trisilicate, polyvinylpyrrolidone, polyacrylate, wax, polyethylene-polyoxypropylene-block polymer, lanolin, sugar (such as lactose, glucose, sucrose, and mannitol), starch (such as cornstarch and potato starch), cellulose and its derivatives (such as sodium carboxymethylcellulose, ethylcellulose and cellulose acetate), powdered gum tragacanth, malt, gelatin, talc, excipient (such as cocoa butter and suppository wax), oil (such as peanut oil, cottonseed oil, safflower oil, sesame oil, olive oil, corn oil and soybean oil), diols (such as propylene glycol and polyethylene glycol), esters (such as ethyl oleate and ethyl laurate), agar, alginic acid, isotonic saline, Ringer's solution, alcohol (such as ethanol, isopropanol, cetyl alcohol, and glycerol), cyclodextrin (such as hydroxypropyl β-cyclodextrin and sulfobutyl ether β-cyclodextrin), lubricant (such as sodium lauryl sulfate and magnesium stearate), and petroleum hydrocarbon (mineral oil and paraffin oil). Colorants, release agents, coating agents, sweetening, flavoring and perfuming agents, preservatives and antioxidants may also be present in the composition, at the discretion of the formulator.

The pharmaceutical composition in the embodiments of the present disclosure may be prepared by methods well known in the art, such as granulation, mixing, dissolving, encapsulation, lyophilization, or emulsification. The pharmaceutical composition may be produced in various forms, including granules, precipitates or microparticles, powders (including freeze-dried, spin-dried or spray-dried powders, amorphous powders), tablets, capsules, syrups, suppositories, injections, emulsions, elixirs, suspensions or solutions. The pharmaceutical composition may be administered by injection or orally.

An embodiment of the present disclosure further provides a method for regulating a glucagon receptor in a subject, including administering the foregoing glucagon receptor antagonist in a dose that inhibits the glucagon receptor to a subject in need thereof.

An embodiment of the present disclosure further provides a method for regulating a glucagon receptor in a subject, including administering the foregoing pharmaceutical composition in a dose that inhibits the glucagon receptor to a subject in need thereof.

The subject is a mammal, further, a human.

An embodiment of the present disclosure further provides a method for regulating blood sugar levels in a subject, including administering the foregoing glucagon receptor antagonist in a dose that inhibits the glucagon receptor to a subject in need thereof.

An embodiment of the present disclosure further provides a method for regulating blood sugar levels in a subject, including administering the foregoing pharmaceutical composition in a dose that inhibits the glucagon receptor to a subject in need thereof.

An embodiment of the present disclosure further provides use of the foregoing glucagon receptor antagonist in preparing drugs for treating diabetes or other diseases associated with dysregulation of glucagon metabolism.

The diseases associated with dysregulation of glucagon metabolism include, but are not limited to, diabetes (type I diabetes or type II diabetes), hyperglycemia, hyperinsulinemia, β-cell rest, abnormal β-cell function (that is, the compound can improve β-cell function by restoring the initial response), dietary hyperglycemia, apoptosis (that is, the compound can prevent apoptosis), impaired fasting glucose (IFG), metabolic syndrome, hypoglycemia, hyper/hypokalemia, disorder of glucagon levels (that is, the compound can normalize glucagon levels), dysregulation of the LDL/HDL ratio (that is, the compound can improve the LDL/HDL ratio), less snacks, eating disorder, weight loss, polycystic ovary syndrome (PCOS), obesity caused by diabetes, latent autoimmune diabetes (potentially admitted autoimmune diabetes, LADA), insulitis, islet transplantation, childhood diabetes, gestational diabetes, late complications of diabetes, micro/macro proteinuria, kidney disease, retinopathy, neuropathy, diabetic foot ulcers, decreased bowel motility due to glucagon administration, broken bowel syndrome, antidiarrhea, increased gastric secretion, decreased blood flow, erectile dysfunction, glaucoma, post-operative stress, organ tissue damage caused by blood reperfusion after ischemia (that is, the compound can ameliorate organ tissue damage caused by blood reperfusion after ischemia), ischemic heart injury, insufficiency of heart function, congestive heart failure, stroke, myocardial infarction, arrhythmia, premature infant death, anti-apoptotic, wound healing, impaired glucose tolerance (IGT), insulin resistance syndrome, syndrome X, hyperlipidemia, dyslipidemia, hypertriglyceridemia, hyperlipoproteinemia, hypercholesterolemia, arteriosclerosis, and the like.

In another exemplary embodiment, screening may be carried out by a method for predicting an antagonist based on artificial intelligence to determine whether the glucagon receptor antagonist is the compound A1 or the compound A2.

The following specifically describes the method for predicting an antagonist based on artificial intelligence.

Figure 6:
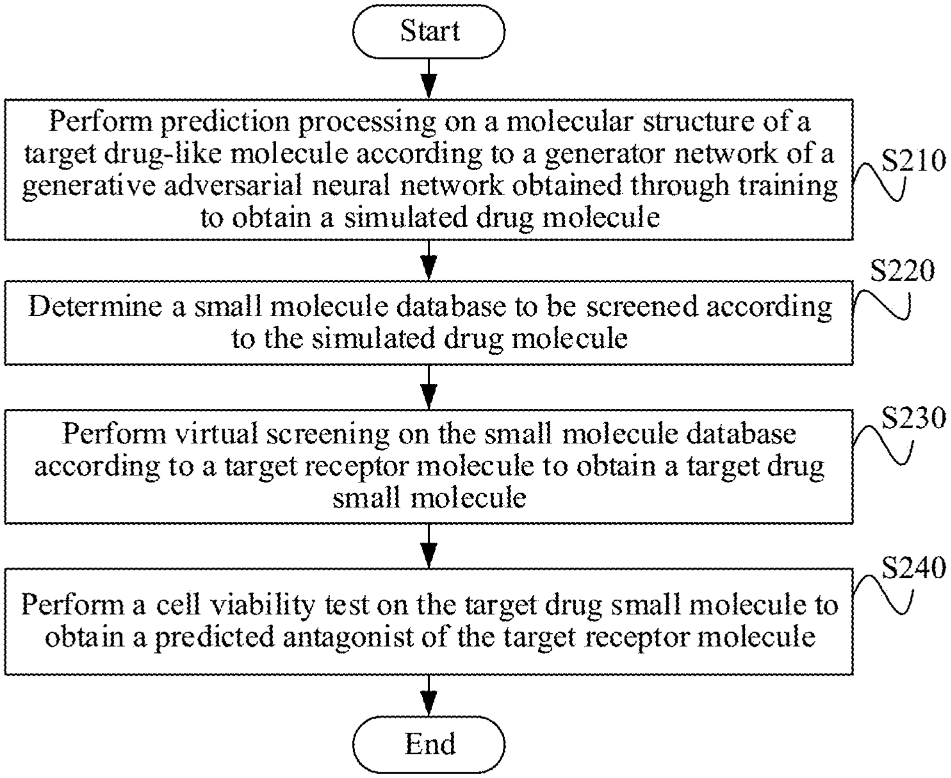
FIG. 6 is a schematic flowchart of a method for predicting an antagonist based on artificial intelligence according to an exemplary embodiment of the present disclosure.

FIG. 6 is a schematic flowchart of a method for predicting an antagonist based on artificial intelligence according to an exemplary embodiment of the present disclosure. The method for predicting an antagonist based on artificial intelligence provided in this embodiment includes the following steps.

Step S210. Perform prediction processing on a molecular structure of a target drug-like molecule according to a generator network of a generative adversarial neural network obtained through training to obtain a simulated drug molecule. The generative adversarial neural network is trained according to a drug-like molecule and an existing antagonist corresponding to a target receptor molecule.

For example, the drug-like molecule and the existing antagonist corresponding to the target receptor molecule are used as a training sample of the generative adversarial neural network. The drug-like molecule in the training sample is inputted to the generator network in the generative adversarial neural network, and a molecular structure of the drug-like molecule is predicted based on the generator network, to obtain a predicted drug molecule. The predicted drug molecule, the drug-like molecule, and the existing antagonist are inputted to a discriminator network in the generative adversarial neural network, and parameters of the generative adversarial neural network are optimized according to an output of the discriminator network of the generative adversarial neural network, to obtain the trained generative adversarial neural network.

Based on the generative adversarial neural network obtained through training, a chemical formula of a target drug-like molecule is acquired for graph encoding to obtain corresponding graph representation, the graph representation corresponding to the target drug-like molecule is inputted into the generator network of the generative adversarial neural network obtained through training, a molecular structure is predicted based on the generator network of the generative adversarial neural network obtained through training, and graph representation of the simulated drug molecule.

Step S220. Determine a small molecule database to be screened according to the simulated drug molecule.

For example, the two-dimensional simulated drug molecule is converted into a three-dimensional molecule by means of force field transformation of chemical simulation software, so as to obtain a small molecule database to be used as a drug database for virtual screening.

Step S230. Perform virtual screening on the small molecule database according to a target receptor molecule to obtain a target drug small molecule.

For example, using the target receptor molecule as a target, according to the shape characteristics, size characteristics, and electrostatic characteristics of a protein active pocket of the target, the affinity between the drug molecule in the small molecule database and the target is calculated by using an optimized search algorithm, and the target drug small molecule is screened out of the small molecule database as the target, that is, the target drug small molecule, corresponding to the target receptor molecule according to the affinity.

Step S240. Perform a cell viability test on the target drug small molecule to obtain a predicted antagonist of the target receptor molecule.

In the solution for predicting an antagonist based on artificial intelligence provided in the embodiment of FIG. 6, on the one hand, the simulated drug molecule of the target receptor molecule is acquired based on a deep learning model, to increase the diversity of the chemical space structure of the simulated drug molecule, so that the skeleton structure of the antagonist determined according to the simulated drug molecule is quite different from the skeleton structure of the existing drug, which is beneficial to improving the diversity of drugs. On the other hand, the small molecule database to be screened is determined according to the simulated drug molecule, and virtual screening is performed on the small molecule database according to the target receptor molecule, so that the target drug small molecule can directly search for a proper conformation in the protein active pocket of the target receptor, which is beneficial to ensuring the appropriateness of the designed antagonist.

The following exemplary embodiment is described by using human glucagon as the target receptor molecule. Certainly, the target receptor molecule may alternatively be a receptor of a characteristic type, which is not limited herein.

Figure 7:
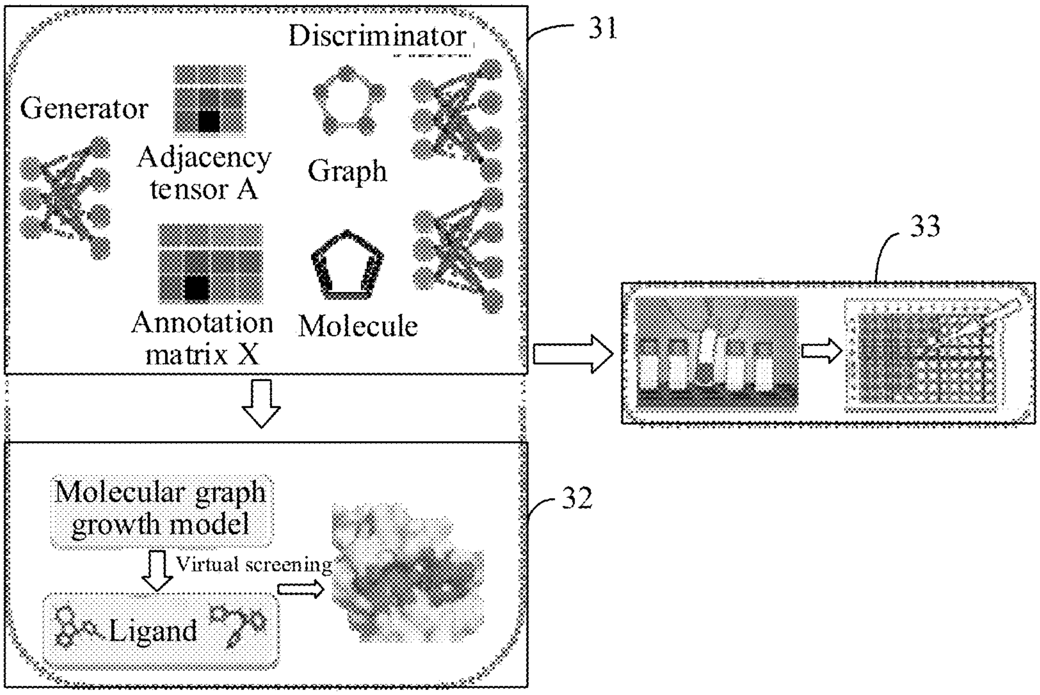
FIG. 7 is a schematic flowchart of a method for predicting an antagonist based on artificial intelligence according to another exemplary embodiment of the present disclosure.

FIG. 7 is a schematic flowchart of a method for predicting an antagonist based on artificial intelligence according to another exemplary embodiment of the present disclosure. Referring to FIG. 7, the method for predicting an antagonist includes: a part 31 of simulated drug molecule acquisition, a part 32 of virtual screening of simulated drug molecule, and a part 33 of viability test on screened target drug small molecule. The part 31 of simulated drug molecule acquisition may be determined based on a generative adversarial network (GAN) obtained through training. For example, graph encoding is performed based on a chemical formula of a drug-like molecule to obtain graph representation corresponding to the drug-like molecule. For example, atoms are represented as points on the graph, and covalent bonds are represented as lines connecting the points. The graph representation corresponding to the drug-like molecule is inputted to a generator network of the GAN obtained through training, and the generator network of the GAN obtained through training may output graph representation corresponding to a simulated drug molecule.

In an exemplary embodiment, a network structure of GAN used in an exemplary embodiment of the present disclosure is first described. For example, FIG. 8 and FIG. 9 respectively show network structures of a generator network and a discriminator network of GAN according to an embodiment of the present disclosure.

Figure 8:
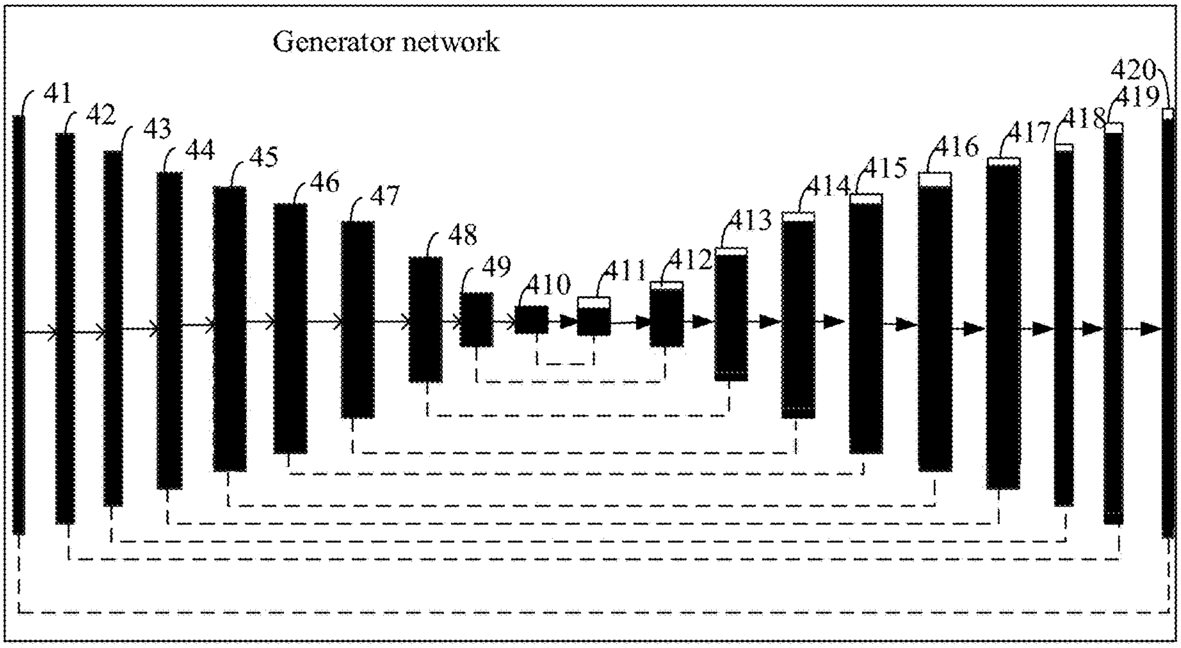
FIG. 8 is a schematic structural diagram of a generator network of an adversarial neural network according to an exemplary embodiment of the present disclosure.

Referring to FIG. 8, the generator network provided in this embodiment may include a convolution layer, a pooling layer, a feature supplementation layer, a deconvolution layer, and a feature normalization layer. In the neural network architecture, a convolution operation and a pooling operation may be used for extracting deep features of the graph representation of the drug-like molecule to learn a logical topological relationship in a molecular graph through the deep features. For example, the vertices of the molecular graph represent atoms, and the side lengths of the molecular graph represent the bond lengths of the molecule. The change rules of vertex and side length, and the relationship between vertex and side length are learned through model training. However, compared with the inputted graph representation of the drug-like molecule, multiple convolution operations and pooling operations reduce the feature image of the molecular graph, resulting in information loss. Therefore, in order to reduce the loss of information, for each down-sampling (such as 41-410 in FIG. 8), a corresponding up-sampling (that is, the feature supplementation layer and the deconvolution layer, such as 411-420 in FIG. 8) is performed. As a result, in the generator network, the up-sampling parameters correspond to the down-sampling parameters, so that the image is reduced in the up-sampling stage, and the corresponding image is enlarged in the down-sampling stage. That is, the generator network adopts the Unet network structure (the dotted line in the shape of "U" in FIG. 8) to reduce the loss of original information during network transmission, thereby reducing the phenomenon that the image content outputted by the generator network is inconsistent with the image content inputted to the generator network due to the mismatch between the down-sampling parameters and the up-sampling parameters, and finally increasing the prediction accuracy of the simulated drug molecule.

In an exemplary embodiment, in the generator network in FIG. 8, the tan h function may be used as an activation function. For example, the output data of the up-sampling 420 may be mapped between −1 and 1 through the tan h function.

Figure 9:
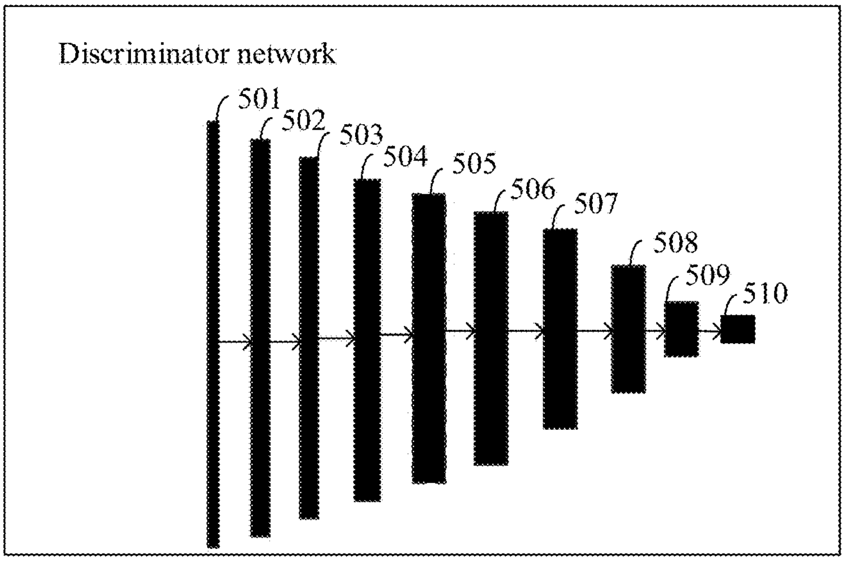
FIG. 9 is a schematic structural diagram of a discriminator network of an adversarial neural network according to an exemplary embodiment of the present disclosure.

In an exemplary embodiment, referring to FIG. 9, a discriminator network of GAN provided in an exemplary embodiment of the present disclosure includes a plurality of convolution layers (such as 501-510 in FIG. 9). Wasserstein GAN (WGAN) may be used in this exemplary technical solution, so the discriminator network does not use the sigmoid function as the activation function in the down-sampling 510, thereby effectively avoiding the loss gradient of the generator network from disappearing.

In an exemplary embodiment, FIG. 8 and FIG. 9 only schematically show network structures of a generator network and a discriminator network. In actual operation, the network structure may be adjusted according to actual needs, so the network structure of the neural network for generating the simulated drug molecule in the present disclosure has scalability.

Figure 10:
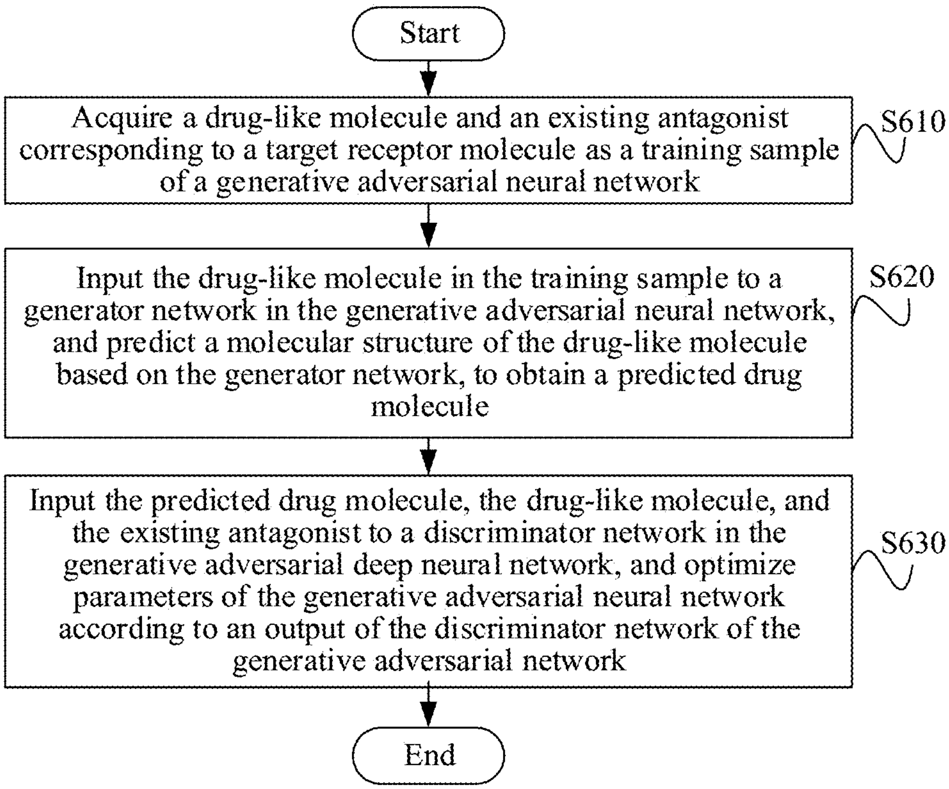
FIG. 10 is a schematic flowchart of a method for training a generator network of an adversarial neural network according to an exemplary embodiment of the present disclosure.

Based on the network structure of WGAN, FIG. 10 is a schematic flowchart of a method for training an adversarial neural network according to an exemplary embodiment of the present disclosure, including steps S610 to S630.

Step S610. Acquire a drug-like molecule and an existing antagonist corresponding to a target receptor molecule as a training sample of an adversarial neural network.

For example, when the target receptor molecule is a human glucagon receptor (hGCGR for short), an existing antagonist of hGCGR is acquired, such as an antagonist that has been reported; and a large number of drug-like molecules are acquired, for example, 1 million drug-like molecules are acquired in a commercial or open-source small molecule database (such as ZINC). The existing antagonist of hGCGR and the 1 million drug-like molecules are used as a training sample set.

Before the training sample is inputted to WGAN, graph encoding is first performed on the training sample to obtain corresponding graph representation. For example, in order to facilitate the processing in WGAN, the drug-like molecules and the existing antagonist in the training sample set are subjected to graph encoding one by one by means of adjacency tensor A and annotation matrix X. For example, the carbon atoms of a cyclopentane may be encoded as the vertices of a pentagon, and the sides of the pentagon correspond to the covalent bonds of the cyclopentane molecule (as shown in the part 31 of simulated drug molecule acquisition in FIG. 7).

Step S620. Input the drug-like molecule in the training sample to a generator network in the generative adversarial neural network, and predict a molecular structure of the drug-like molecule based on the generator network, to obtain a predicted drug molecule.

Figure 11:
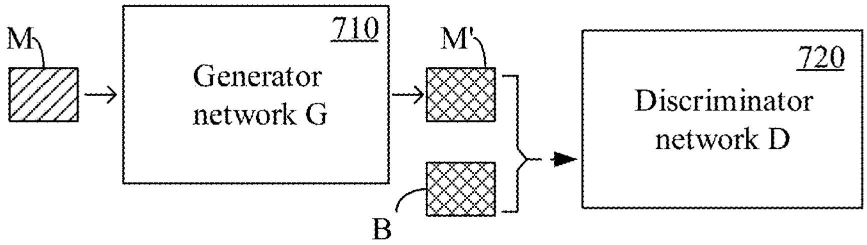
FIG. 11 is a schematic flowchart of a method for training a generator network of an adversarial neural network according to another exemplary embodiment of the present disclosure.

In an exemplary embodiment, FIG. 11 is a schematic framework diagram of a model training method according to an embodiment of the present disclosure. Referring to FIG. 11, the generative adversarial deep neural network includes a generator network G 710 and a discriminator network D 720.

The generator network G 710 is configured to perform prediction processing (such as convolution processing, deconvolution processing, and normalization processing) on a molecular structure of a drug-like molecule M (specifically, graph representation corresponding to the drug-like molecule M). An output of the generator network G 710 is a predicted drug molecule M' (specifically, graph representation corresponding to the predicted drug molecule M'). The generator network G 710 is trained to: perform prediction processing on the molecular structure of the drug-like molecule M to obtain the predicted drug molecule that makes the discrimination result of the discriminator network D 720 "true". That is, the discriminator network D 720 predicts that the probability that the predicted drug molecule M' is the antagonist of the target receptor molecule is greater than 0.5. That is, the generator network G 710 is trained to make the predicted drug molecule closer to the existing antagonist, so as to achieve an effect of "passing fake off as real" (the discriminator D 720 determines that the predicted drug molecule M' is the antagonist of the target receptor molecule as "true").

Figure 12:
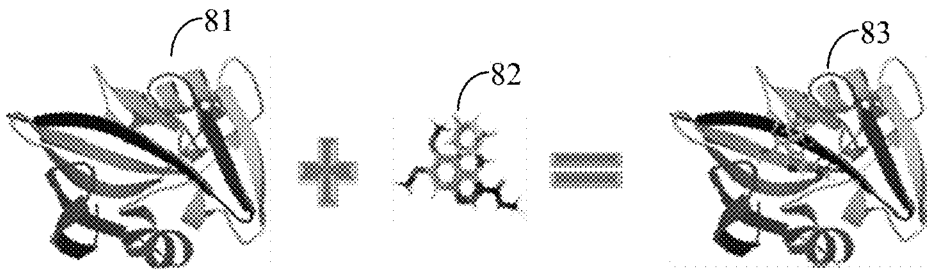
FIG. 12 is a schematic flowchart of a virtual screening method according to an exemplary embodiment of the present disclosure.

Further refer to FIG. 12. Step S630. Input the predicted drug molecule, the drug-like molecule, and the existing antagonist to a discriminator network in the generative adversarial deep neural network, and optimize parameters of the generative adversarial neural network according to an output of the discriminator network of the generative adversarial network.

In an exemplary embodiment, the predicted drug molecule M' (specifically the graph representation corresponding to the predicted drug molecule M') and the existing antagonist B (specifically the graph representation corresponding to the existing antagonist B) are inputted to the discriminator network D 720 to determine whether the predicted drug molecule M' is the antagonist of the target receptor molecule through the discriminator network D 720. For example, if the discriminator network D 720 determines that the predicted drug molecule M' is the antagonist of the target receptor molecule, indicating that the predicted drug molecule M' generated by the current generator has a high accuracy (that is, it can achieve an effect of "passing fake off as real"), then the optimization of the parameters of the generator network can be stopped. If the discriminator network D 720 determines that the predicted drug molecule M' is not the antagonist of the target receptor molecule, indicating that the predicted drug molecule M' generated by the current generator has an accuracy to be further increased (that is, it cannot achieve an effect of "passing fake off as real" so far), then the optimization of the parameters of the generator network needs to be continued.

In another exemplary embodiment, the output of the discriminator network includes a first discrimination result on the predicted drug molecule and a second discrimination result on the existing antagonist. The first discrimination result includes a probability that the predicted drug molecule M' outputted by the discriminator network is the antagonist of the target receptor molecule. The second discrimination result includes a probability that the existing antagonist B outputted by the discriminator network is the antagonist of the target receptor molecule.

In an exemplary embodiment, further referring to FIG. 11, the discriminator network D 720 is configured to receive the predicted drug molecule M' (specifically the graph representation corresponding to the predicted drug molecule M') and the existing antagonist B (specifically the graph representation corresponding to the existing antagonist B). The discriminator network D 720 determines the probability that the predicted drug molecule M' is the antagonist of the target receptor molecule (that is, the first discrimination result) through a difference between the predicted drug molecule M' and the existing antagonist B. If the probability is greater than 0.5, the first discrimination result is that: the predicted drug molecule M' is the antagonist of the target receptor molecule, that is, the discrimination result outputted by the discriminator network is that: the predicted drug molecule M' is "true". Correspondingly, if the probability is not greater than 0.5, the first discrimination result is that: the predicted drug molecule M' is not the antagonist of the target receptor molecule, that is, the discrimination result outputted by the discriminator network is that: the predicted drug molecule M' is "false".

In addition, the discriminator network D 720 also predicts the probability that the existing antagonist B is the antagonist of the target receptor molecule (that is, the second discrimination result). If the probability is greater than 0.5, the second discrimination result is that: the existing antagonist B is the antagonist of the target receptor molecule, that is, the discrimination result outputted by the discriminator network is that: the existing antagonist B is "true". Correspondingly, if the probability is not greater than 0.5, the second discrimination result is that: the existing antagonist B is not the antagonist of the target receptor molecule, that is, the discrimination result outputted by the discriminator network is that: the existing antagonist B is "false".

The discriminator network D 720 is trained to: discriminate that the existing antagonist is "true" (the probability of the second discrimination result is greater than 0.5), and discriminate that the predicted drug molecule is "false" (the probability of the first discrimination result is not greater than 0.5).

In an exemplary embodiment, the parameters of the generative adversarial neural network are optimized according to the first discrimination result and the second discrimination result.

In an exemplary embodiment, further referring to FIG. 11, the first discrimination result and the second discrimination result are determined according to a logical topological difference between the predicted drug molecule M' and the existing antagonist B, and the parameters of the generator network G 710 and the parameters of the discriminator network D 720 are optimized according to the first discrimination result and the second discrimination result. For example, a loss function is represented by the formula (1):

$$\text{Loss} = \frac{1}{m}\sum_{i=1}^{m}\left[\log D(x^i) + \log\left(1 - D\left(G(z^i)\right)\right)\right] \quad (1)$$

$x^i$ and $z^i$ respectively represent data corresponding to the existing antagonist B and data corresponding to the predicted drug molecule M', D represents the discriminator network D, G represents the generator network G, i is a positive integer that is not greater than m, and m is a sample number.

The loss function is optimized to $\min_G \max_G$ Loss. First, the parameters of the generator network G are fixed, and the parameters of the discriminator network D are adjusted. For example, the parameters of the discriminator D are optimized by the formula 2:

$$\max_D\text{Loss} = \frac{1}{m}\sum_{i=1}^{m}\left[\log D(x^i) + \log\left(1 - D\left(G(z^i)\right)\right)\right] \quad (2)$$

$D(x^i)$ represents the second discrimination result (that is, the probability that the existing antagonist B is the antagonist of the target receptor molecule), the larger the value is, the better. $D(G(z^i))$ represents the first discrimination result (that is, the probability that the predicted drug molecule A' is the antagonist of the target receptor molecule), the smaller the value is, the better (that is, the larger log $(1-D(G(z^i)))$ is, the better).

For example, through $\max_D$ Loss, the first discrimination result outputted by the discriminator network D is that: the probability that the predicted drug molecule M' is the antagonist of the target receptor molecule is not greater than 0.5; and the second discrimination result is that: the probability that the existing antagonist B is the antagonist of the target receptor molecule is greater than 0.5.

Then, the parameters of the discriminator D are fixed, and the parameters of the generator network G are adjusted. Since the generator network G does not involve the processing of the existing antagonist B (the corresponding data is $x^i$), log $D(x^i)$ is not involved in the process of optimizing the parameters of the generator network G. Specifically, the parameters of the generator G are optimized by the formula 3:

$$\min_G\text{Loss} = \frac{1}{m}\sum_{i=1}^{m}\log\left(1 - D\left(G(z^i)\right)\right) \quad (3)$$

$D(G(z^i))$ represents the first discrimination result (that is, the probability that the predicted drug molecule A' is the antagonist of the target receptor molecule), the larger the value is, the better (that is, the smaller log $(1-D(G(z^i)))$ is, the better).

For example, after the predicted drug molecule A' outputted by the generator G with the parameters adjusted is inputted to the discriminator D through $\min_G$ Loss, the first discrimination result outputted by the discriminator D is that: the probability that the predicted drug molecule A' is the antagonist of the target receptor molecule is greater than 0.5.

After continuous iterative calculation, the above loss value satisfies a preset requirement. In addition, the generator network G (also referred to as molecular graph growth model) of GAN obtained through training may grow a simulated drug molecule that is similar to that in the training set.

In an exemplary embodiment, when the model prediction is performed by using WGAN, an earth mover (EM) distance may be used as a loss function. Since the log value is no longer calculated in the loss function, the training can be more easily converged.

The specific implementation of determining the simulated drug molecule based on the molecular graph growth model obtained through training (that is, the generator network of GAN or WGAN obtained through training) is as follows. A chemical formula of a target drug-like molecule is acquired for graph encoding to obtain corresponding graph representation; and the graph representation corresponding to the target drug-like molecule is inputted into the molecular graph growth model, and a molecular structure is predicted based on the molecular graph growth model, to output graph representation of the simulated drug molecule.

The molecular graph growth model outputs the graph representation corresponding to the simulated drug molecule. In order to facilitate the subsequent virtual screening, decoding processing needs to be performed to obtain a standard format of the simulated drug molecule, such as a linear symbol for inputting and representing a molecular reaction (simplified molecular input line entry system, SMILES) and a structure data file (SDF).

Therefore, the encoded simulated drug molecule outputted by the molecular graph growth model is decoded to obtain the chemical formula of the simulated drug molecule that satisfies a preset format.

Further referring to FIG. 7, after the part 31 of simulated drug molecule acquisition, there is the part 32 of virtual screening of simulated drug molecule. The following describes the embodiment of virtual screening of the simulated drug molecule.

For example, further referring to FIG. 6, in step S220, a small molecule database to be screened is determined according to the simulated drug molecule; and in step S230, virtual screening is performed on the small molecule database according to a target receptor molecule to obtain a target drug small molecule.

The small molecule database is a database for virtual screening. For example, 10 million simulated drug molecules are generated by using the molecular graph growth model and decoded to obtain standard formats of these simulated drug molecules. In order to search for a proper conformation in the protein active pocket by the simulated drug molecule directly, it is necessary to convert the simulated drug molecule into a three-dimensional simulated drug molecule (for example, a mol2 format). In an exemplary embodiment, the two-dimensional simulated drug molecule is converted into a three-dimensional molecule by means of force field transformation of chemical simulation software, so as to obtain the small molecule database to be used as a drug database for virtual screening.

In an exemplary embodiment, for comparison, 100,000 non-simulated drug molecules may be randomly selected from an existing database (for example, the ChemBridge database). The non-simulated drug molecules are merged into the small molecule database to be used as a drug database for virtual screening.

In an exemplary embodiment, in view of the principle of virtual screening, candidate compounds that can be used as targets are screened out of the small molecule database according to the shape characteristics, size characteristics, and electrostatic characteristics of the protein active pocket of the target (target receptor molecule). Therefore, before virtual screening is performed on the new molecular database, in order to ensure the smooth progress of the virtual screening, the target receptor molecule needs to be preprocessed, such as completion of amino acid residues in the target receptor molecule, hydrogenation of the target receptor molecule, and charging of the target receptor molecule.

For example, the human glucagon receptor molecule hGCGR (number: 5EE7) is downloaded from an existing database (such as the PDB database) as the target receptor molecule. The hGCGR is preprocessed as follows. The amino acid residues of the hGCGR protein molecule are completed by using the Schrödinger software, the target receptor molecule hGCGR is subjected to hydrogenation and charging, and the preprocessed hGCGR protein molecule is saved in a three-dimensional format (for example, mol2 format).

In order to ensure the smooth progress of the virtual screening, the format of the target receptor molecule and the format of the drug molecule in the small molecule database are unified, for example, they are unified into the mol2 format.

In an exemplary embodiment, referring to FIG. 12, based on the molecular docking technology, a virtual screening process is performed on the small molecule database and the target receptor molecule in the three-dimensional format. The molecular docking technology is based on the principle of the "lock and key" model. A receptor protein 81 is equivalent to a "lock", and a small molecule 82 is equivalent to a "key". The virtual screening is implemented by whether the two can be combined into 83. For example, using the target receptor molecule hGCGR as a target, according to the shape characteristics, size characteristics, and electrostatic characteristics of a protein active pocket of the target, the affinity between the drug molecule in the small molecule database and the target is calculated by using an optimized search algorithm, and the target drug small molecule is screened out of the small molecule database as the target, that is, the candidate compound, corresponding to the target receptor molecule hGCGR according to the affinity.

For example, depending on whether a small molecule in the small molecule database is a potential target drug, each small molecule is scored through a scoring function, the small molecules are sorted in descending order according to the scores, and the first multiple (for example, 30) small molecules in a descending sorting result are used as the target drug small molecules, see Table 2.

TABLE 2

| Number | SMILES sequence of target drug small molecule |
| --- | --- |
| C1 | NS(=O)(=O)c1ccc(NC(=S)NNC(=S)NC2CCCCC2)cc1 |
| | 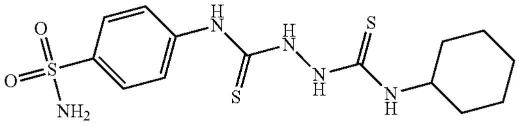 [SMILES: NS(=O)(=O)c1ccc(NC(=S)NNC(=S)NC2CCCCC2)cc1] |
| C2 | O=S(=O)(NCCc1ccccc1)c1ccc(NC(=S)Nc2ccccc2)cc1 |
| | 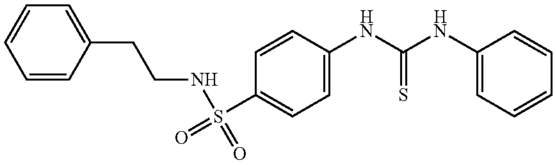 [SMILES: O=S(=O)(NCCc1ccccc1)c1ccc(NC(=S)Nc2ccccc2)cc1] |
| C3 | COc1ccc(C(=O)NC(=S)Nc2ccc(NC(=S)NC(C)=O)cc2)cc1Cl |
| | 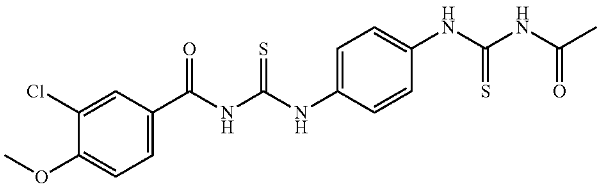 [SMILES: COc1ccc(C(=O)NC(=S)Nc2ccc(NC(=S)NC(C)=O)cc2)cc1Cl] |
| C4 | O=S(=O)(Nc1ccc(Cl)cc1)c1ccc(NC(=S)Nc2ccccc2)cc1 |
| | 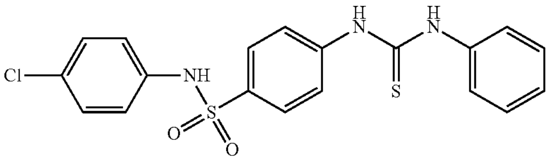 [SMILES: O=S(=O)(Nc1ccc(Cl)cc1)c1ccc(NC(=S)Nc2ccccc2)cc1] |
| C5 | O=C(NCCCCCCNC(=O)NCc1cccnc1)NCc1cccnc1 |

TABLE 2-continued
| Number | SMILES sequence of target drug small molecule |
| --- | --- |
| | 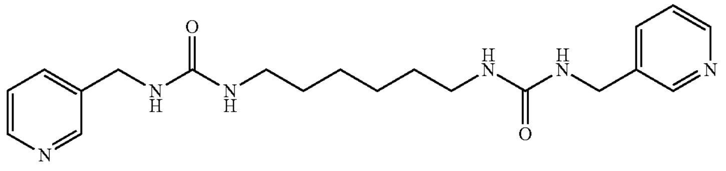 [SMILES: O=C(NCCCCCCNC(=O)NCc1cccnc1)NCc1cccnc1] |
| C6 | O=C(CCCCC(=O)NNC(=S)Nc1ccc(Br)cc1)NNC(=S)Nc1ccc(Br)cc1 |
| | 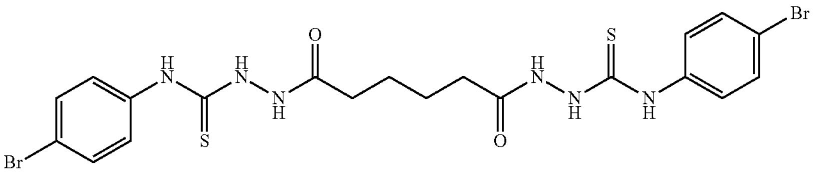 [SMILES: O=C(CCCCC(=O)NNC(=S)Nc1ccc(Br)cc1)NNC(=S)Nc1ccc(Br)cc1] |
| C7 | O=C(NNC(=S)Nc1ccccc1)[C@H](O)[C@@H](O)C(=O)NNC(=S)Nc1ccccc1 |
| | 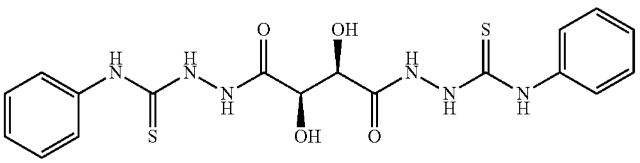 [SMILES: O=C(NNC(=S)Nc1ccccc1)[C@H](O)[C@@H](O)C(=O)NNC(=S)Nc1ccccc1] |
| C8 | CCC(=O)NC(=S)Nc1ccc(NC(=S)NC(=O)c2ccccc2OC)cc1 |
| | 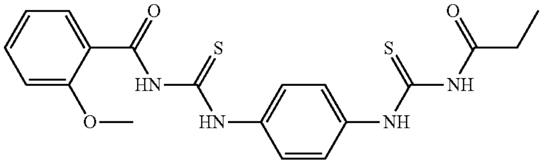 [SMILES: CCC(=O)NC(=S)Nc1ccc(NC(=S)NC(=O)c2ccccc2OC)cc1] |
| C9 | CCC(=O)NC(=S)Nc1ccc(NC(=S)NC(=O)c2cccc(OC)c2)cc1 |
| | 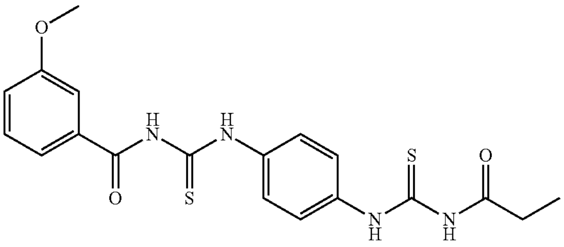 [SMILES: CCC(=O)NC(=S)Nc1ccc(NC(=S)NC(=O)c2cccc(OC)c2)cc1] |
| C10 | CN1C(=O)Cc2cc(S(=O)(=O)CCC(=O)NCCc3ccccc3)ccc21 |
| | 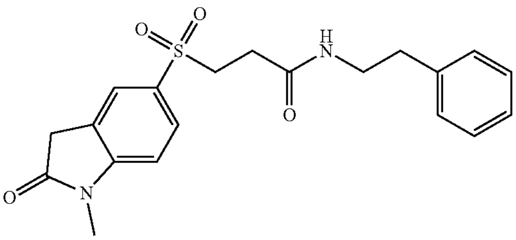 [SMILES: CN1C(=O)Cc2cc(S(=O)(=O)CCC(=O)NCCc3ccccc3)ccc21] |
| C11 | CC(=O)c1ccccc1NC(=O)c1c(O)c2c3c(sc2[nH]c1=O)C[C@H](C)CC3 |

TABLE 2-continued
| Number | SMILES sequence of target drug small molecule |
| --- | --- |
| | 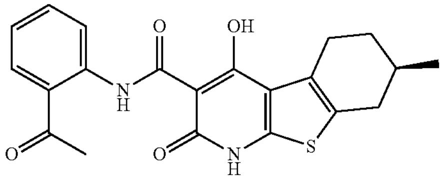 [SMILES: CC(=O)c1ccccc1NC(=O)c1c(O)c2c3c(sc2[nH]c1=O)C[C@H](C)CC3] |
| C12 | COc1cc(/C=N/NC(=O)CN2C(=O)N[C@H]3NC(=O)N[C@@H]32)cc(OC)c1O |
| | 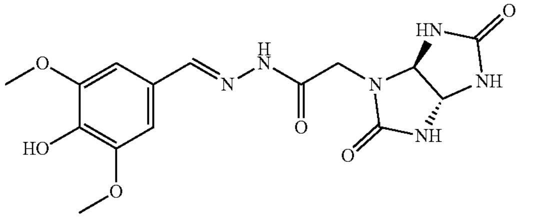 [SMILES: COc1cc(/C=N/NC(=O)CN2C(=O)N[C@H]3NC(=O)N[C@@H]32)cc(OC)c1O] |
| C13 | COc1ccc(NC(=O)c2c(O)c3c4c(sc3[nH]c2=O)C[C@@H](C)CC4)cc1Cl |
| | 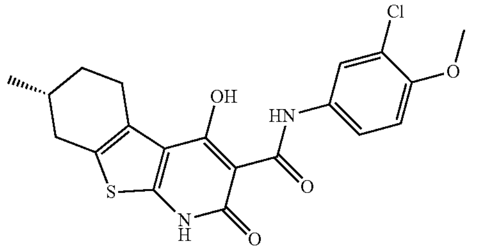 |
| C14 | CSc1cccc(NC(=O)c2c(O)c3sccc3[nH]c2=O)c1 |
| | 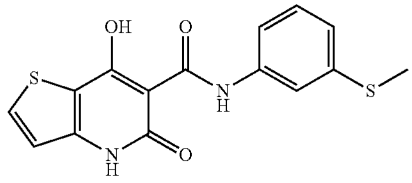 [SMILES: CSc1cccc(NC(=O)c2c(O)c3sccc3[nH]c2=O)c1] |
| C15 | COc1ccc2cc(C(=O)NCCNc3ccc(C)nn3)[nH]c2c1 |
| | 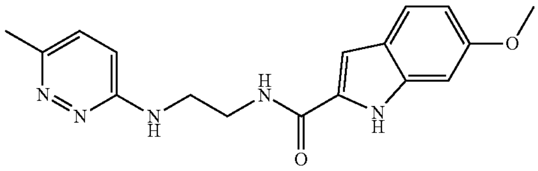 |
| C16 | O=C(CCNC(=O)c1ccccc1)NCc1cccc(NC(=O)C2CC2)c1 |
| | 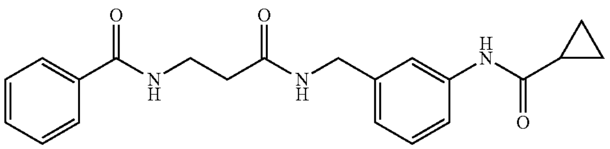 [SMILES: O=C(CCNC(=O)c1ccccc1)NCc1cccc(NC(=O)C2CC2)c1] |
| C17 | CSc1cccc(NC(=O)CCNS(=O)(=O)c2ccc(NC(C)=O)cc2)c1 |

TABLE 2-continued
| Number | SMILES sequence of target drug small molecule |
|---|---|
| | 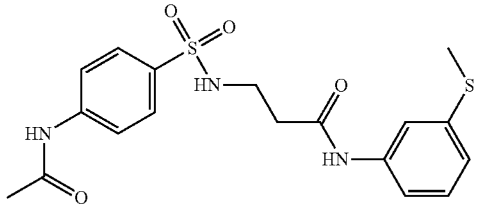 [SMILES: CSc1cccc(NC(=O)CCNS(=O)(=O)c2ccc(NC(C)=O)cc2)c1] |
| C18 | O═C(COC(═O)CCNS(═O)(═O)c1ccc(Cl)cc1)NC(═O)NCc1ccco1 |
| | 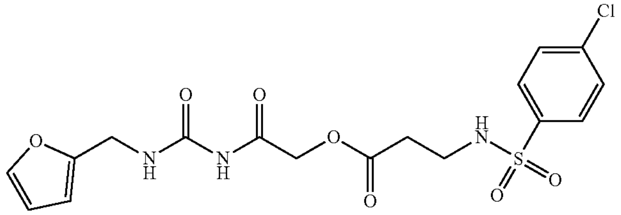 [SMILES: O=C(COC(=O)CCNS(=O)(=O)c1ccc(Cl)cc1)NC(=O)NCc1ccco1] |
| C19 | O═C(CNC(═O)NCCCOC1CCCCC1)Nc1ccc(F)c(F)c1 |
| | 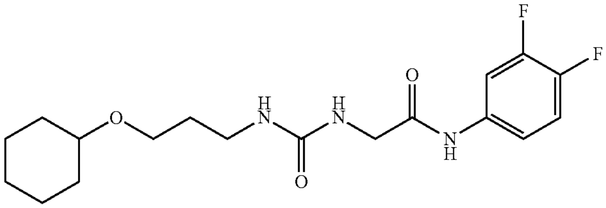 [SMILES: O=C(CNC(=O)NCCCOC1CCCCC1)Nc1ccc(F)c(F)c1] |
| C20 | O═C(COC(═O)CCNC(═O)c1ccsc1)NC(═O)NCc1cccs1 |
| | 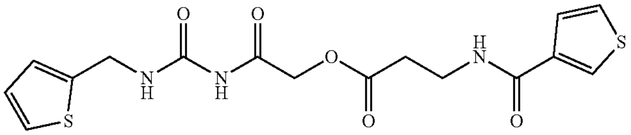 [SMILES: O=C(COC(=O)CCNC(=O)c1ccsc1)NC(=O)NCc1cccs1] |
| C21 | O═C(CSc1nc2ccccc2[nH]1)NC(═O)Nc1ccc2c(c1)OCO2 |
| | 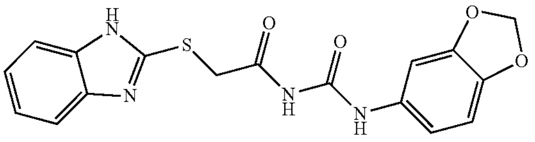 [SMILES: O=C(CSc1nc2ccccc2[nH]1)NC(=O)Nc1ccc2c(c1)OCO2] |
| C22 | O═C(CNC(═O)NCCCN1CCCCCC1═O)Nc1ccc(F)c(F)c1 |
| | 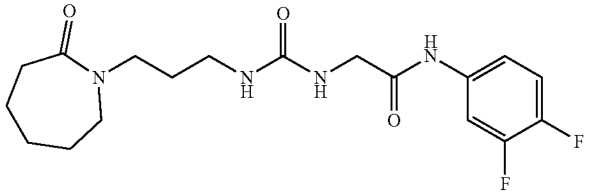 [SMILES: O=C(CNC(=O)NCCCN1CCCCCC1=O)Nc1ccc(F)c(F)c1] |
| C23 | Cc1ccc(-c2csc(NC(═O)c3ccc4c(c3)NC(═O)CS4)n2)c(C)c1 |

TABLE 2-continued
| Number | SMILES sequence of target drug small molecule |
|---|---|
| | 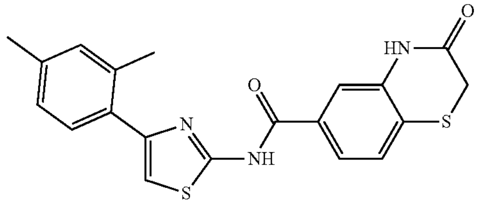 [SMILES: Cc1ccc(-c2csc(NC(=O)c3ccc4c(c3)NC(=O)CS4)n2)c(C)c1] |
| C24 | CNC(=O)Cc1ccccc1NC(=O)NCCC(=O)NC1CCCC1 |
| | 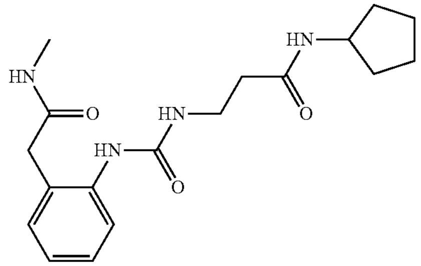 [SMILES: CNC(=O)Cc1ccccc1NC(=O)NCCC(=O)NC1CCCC1] |
| C25 | CC(C)(C)NC(=O)NC(=O)CSc1nc(-c2cccs2)c(-c2cccs2)[nH]1 |
| | 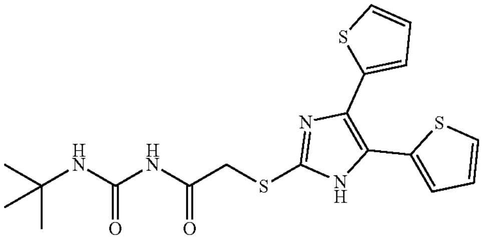 [SMILES: CC(C)(C)NC(=O)NC(=O)CSc1nc(-c2cccs2)c(-c2cccs2)[nH]1] |
| C26 | COc1cc(NC(=O)CNC(=O)CNC(=O)c2cccs2)c(OC)cc1Cl |
| | 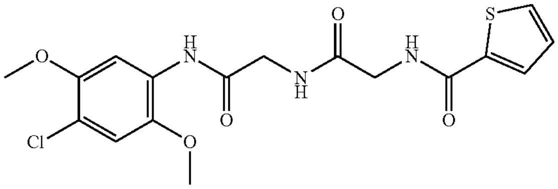 [SMILES: COc1cc(NC(=O)CNC(=O)CNC(=O)c2cccs2)c(OC)cc1Cl] |
| C27 | O=C(CCNC(=O)NC1CCCCC1)NNc1ccccc1C(F)(F)F |
| | 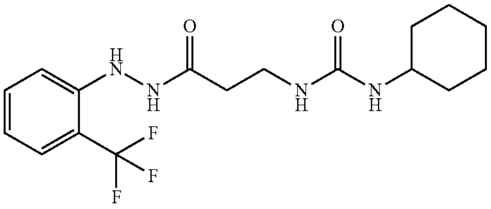 [SMILES: O=C(CCNC(=O)NC1CCCCC1)NNc1ccccc1C(F)(F)F] |
| C28 | CS(=O)(=O)NCCOc1ccc(S(=O)(=O)NCCOc2ccccc2)cc1 |

TABLE 2-continued

| Number | SMILES sequence of target drug small molecule |
| --- | --- |
| | 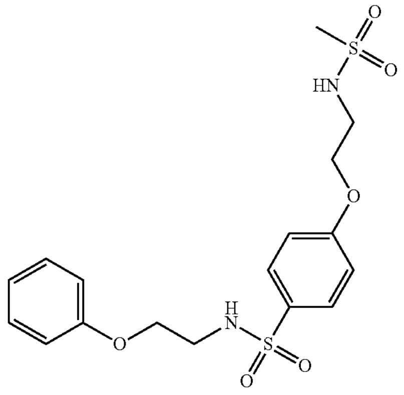 [SMILES: CS(=O)(=O)NCCOc1ccc(S(=O)(=O)NCCOc2ccccc2)cc1] |
| C29 | Cn1c(CNC(=O)c2cccs2)nnc1SCC(=O)Nc1ccc(Cl)cc1 |
| | 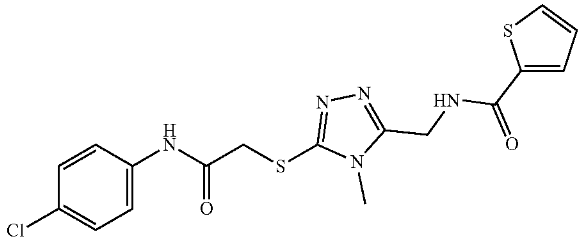 [SMILES: Cn1c(CNC(=O)c2cccs2)nnc1SCC(=O)Nc1ccc(Cl)cc1] |
| C30 | CNC(=O)NC(=O)CSc1nc2cc(-c3ccc(F)cc3)sc2c(=O)n1N |
| | 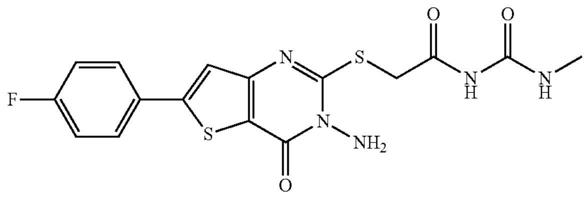 [SMILES: CNC(=O)NC(=O)CSc1nc2cc(-c3ccc(F)cc3)sc2c(=O)n1N] |

C13 in Table 2 is the compound A1, and C14 is the compound A2.

Further referring to FIG. 7, after the part 31 of simulated drug molecule acquisition and the part 32 of virtual screening of simulated drug molecule, there is the part 33 of viability test on screened target drug small molecule (Table 2). The following describes the embodiment of viability test on the screened target drug small molecule.

For example, further referring to FIG. 6, in step S240, a cell viability test is performed on the target drug small molecule to obtain an antagonist of the target receptor molecule.

The target drug small molecules C1-C30 are obtained by outsourcing or synthesis for the following viability test.

Figure 13:
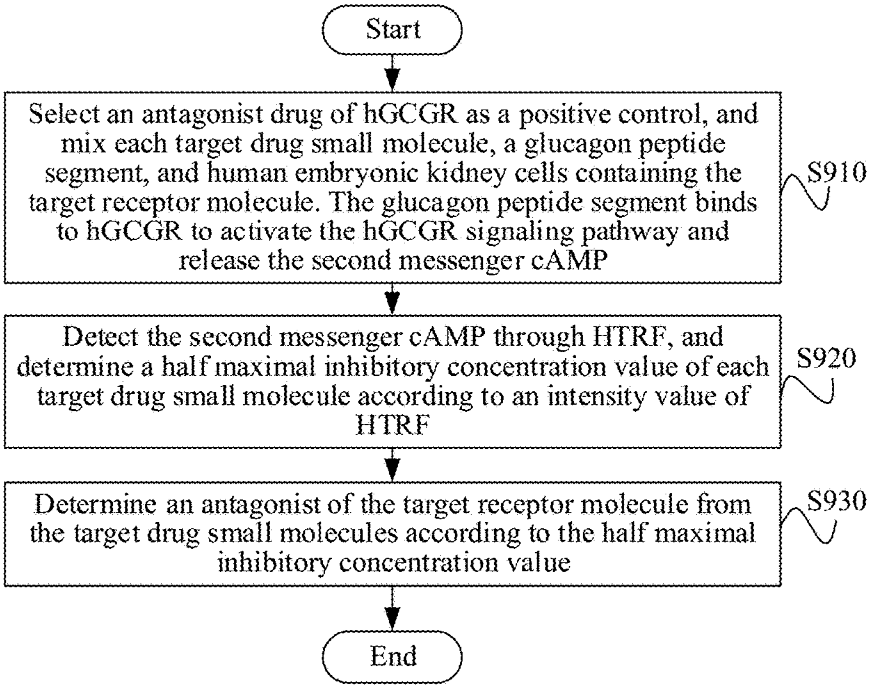
FIG. 13 is a schematic flowchart of an activity detection method of a target compound according to an exemplary embodiment of the present disclosure.

In an exemplary embodiment, when the target receptor molecule is a human glucagon receptor, FIG. 13 shows a specific implementation of performing a cell viability test on the target drug small molecule.

Step S910. Select an antagonist drug of hGCGR as a positive control, and mix each target drug small molecule, a glucagon peptide segment, and human embryonic kidney cells containing the target receptor molecule. The glucagon peptide segment binds to hGCGR to activate the hGCGR signaling pathway and release the second messenger cAMP. The target drug molecule acts as an antagonist to inhibit the activity of hGCGR.

In an exemplary embodiment, an antagonist drug (such as L-168,049) of hGCGR is selected as a positive control. In addition, in view of the human glucagon receptor on the cell membrane of human embryonic kidney cells (such as HEK293), HEK293 may be used to test the drug activity of the human glucagon antagonist. The target drug small molecule, the glucagon peptide segment, and the HEK293 cells containing the target receptor molecule are mixed. The glucagon peptide segment is used to bind to hGCGR to activate the hGCGR signaling pathway and promote the release of the second messenger cAMP. The target drug molecule acts as an antagonist to inhibit the activity of hGCGR.

Step S920. Detect the second messenger cAMP through HTRF, and determine a half maximal inhibitory concentration value of each target drug small molecule according to an intensity value of HTRF.

In an exemplary embodiment, the activity of each target drug small molecule (such as 30 target drug small molecules shown in Table 2) is tested by using the HTRF technique. Specifically, after activation of the glucagon receptor by the glucagon peptide segment, the second messenger cAMP is released from the glucagon receptor cells, the second messenger cAMP may be detected by HTRF, and the half maximal inhibitory concentration (IC50) of the drug molecule may be calculated according to the fluorescence intensity.

Step S930. Determine an antagonist of the target receptor molecule from the target drug small molecules according to the half maximal inhibitory concentration value.

In an exemplary embodiment, for the 30 target drug small molecules shown in Table 2, 11 identical concentration gradients are set for each target drug small molecule. The activity of each target drug small molecule is determined by the HTRF second messenger cAMP response experiment in triplicate. The experimental data obtained is shown in Table 3.

TABLE 3

| Concentration | C1 | | | C2 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | −28.0258 | −21.233 | −13.007 | 3.236993 | 24.94373 | 13.36669 | 100.8895 |
| −5.477121 | −14.4564 | −9.71743 | −14.5956 | 1.776627 | 7.94289 | −25.2765 | 98.1315 |
| −5.954243 | 15.2744 | −5.04528 | 24.07916 | −15.0817 | −15.3237 | 4.391063 | 94.46029 |
| −6.431364 | 9.37852 | −4.14799 | 14.31144 | −0.53168 | −15.9398 | −32.6918 | 88.0059 |
| −6.908485 | −18.9021 | 21.35055 | 4.698388 | −18.7178 | −9.89474 | −3.86237 | 74.79468 |
| −7.385606 | −25.9558 | 3.252519 | −8.77172 | −6.16686 | 15.0145 | −21.4454 | 16.30664 |
| −7.862728 | 17.54573 | −3.01577 | −15.9679 | 9.494435 | −19.3489 | −6.35426 | 15.3532 |
| −8.339849 | 23.35759 | 11.77735 | 18.98269 | −16.8681 | 6.175196 | −11.2756 | −9.20905 |
| −8.81697 | 3.261729 | −32.569 | −19.2486 | 3.217721 | −18.2214 | −23.1148 | −3.66343 |
| −9.294091 | −23.3919 | −4.769 | −10.8733 | 1.325076 | 0.80065 | 5.406518 | −1.83995 |
| −9.771213 | 2.845776 | −32.6062 | −21.4687 | −13.0928 | −15.3836 | −32.7196 | 6.132259 |
| Concentration | C3 | | | C4 | | | L-168,049 |
| gradient LogM | Inhibition percentage | Inhibition percentage | Inhibition percentage | Inhibition percentage | Inhibition percentage | Inhibition percentage | Inhibition percentage |
| −5 | 17.5365 | −19.8571 | 13.07843 | −7.98023 | 18.30761 | 8.109144 | 100.8895 |
| −5.477121 | 7.062952 | −13.1408 | −20.3045 | −21.977 | 3.450386 | −34.0441 | 98.1315 |
| −5.954243 | −27.5202 | −34.2999 | 8.031528 | 23.03118 | 21.855 | −35.0246 | 94.46029 |
| −6.431364 | −14.7068 | 8.213836 | −19.4572 | −17.516 | 29.34127 | 0.099727 | 88.0059 |
| −6.908485 | 5.050306 | 4.704503 | 12.01524 | −34.2076 | −17.0491 | 5.095997 | 74.79468 |
| −7.385606 | −11.469 | −14.3269 | −26.5832 | −10.2779 | −43.5579 | −44.3127 | 16.30664 |
| −7.862728 | −4.82247 | 22.19872 | 37.22665 | −22.7041 | 13.11766 | 14.0343 | 15.3532 |
| −8.339849 | 38.45775 | −11.5852 | 6.377197 | −39.6923 | −37.7534 | −28.0946 | −9.20905 |
| −8.81697 | −37.1112 | 24.86409 | 25.39576 | −29.3017 | 28.12523 | −35.2389 | −3.66343 |
| −9.294091 | −12.3879 | 22.72449 | −24.7055 | −22.7752 | −7.6478 | 10.39849 | −1.83995 |
| −9.771213 | −7.94458 | −38.3808 | −38.8089 | 8.16323 | −15.6864 | −11.0532 | 6.132259 |
| Concentration | C5 | | | C6 | | | L-168,049 |
| gradient LogM | Inhibition percentage | Inhibition percentage | Inhibition percentage | Inhibition percentage | Inhibition percentage | Inhibition percentage | Inhibition percentage |
| −5 | −4.47669 | 2.99794 | 10.59306 | 1.324715 | −19.4427 | −0.59812 | 100.8895 |
| −5.477121 | −8.81744 | 9.731563 | 24.85593 | −7.39909 | −31.1356 | 11.61118 | 98.1315 |
| −5.954243 | −19.0769 | 16.9306 | 32.16685 | 2.828327 | −16.4923 | −14.7246 | 94.46029 |
| −6.431364 | −40.8977 | 36.99523 | 19.7015 | −1.20885 | −33.8383 | −27.1264 | 88.0059 |
| −6.908485 | −11.8532 | 21.80451 | −9.38534 | 22.74271 | −29.6222 | −13.735 | 74.79468 |
| −7.385606 | 2.139664 | −31.8124 | 14.4573 | −10.0239 | 7.609363 | −37.6003 | 16.30664 |
| −7.862728 | 13.23674 | 0.887792 | −7.86726 | −28.7792 | −19.4453 | −24.9236 | 15.3532 |
| −8.339849 | −13.3723 | 0.993211 | 27.5293 | −21.4961 | 2.644305 | −14.7628 | −9.20905 |
| −8.81697 | 20.063 | 2.106405 | 7.734295 | 24.56327 | −7.31118 | −4.04869 | −3.66343 |
| −9.294091 | 5.655235 | 15.5193 | −16.5791 | −8.6768 | −2.92442 | −18.0637 | −1.83995 |
| −9.771213 | 4.21249 | −20.4926 | 12.41512 | −17.3174 | −6.7556 | −19.5629 | 6.132259 |
| Concentration | C7 | | | C8 | | | L-168,049 |
| gradient LogM | Inhibition percentage | Inhibition percentage | Inhibition percentage | Inhibition percentage | Inhibition percentage | Inhibition percentage | Inhibition percentage |
| −5 | 24.68995 | −1.7966 | −19.0029 | −2.87803 | −5.23341 | −26.9314 | 100.8895 |
| −5.477121 | −10.0731 | −17.914 | −39.5885 | −18.766 | −3.18983 | −10.0851 | 98.1315 |
| −5.954243 | −14.3481 | 13.8798 | −23.9423 | −26.881 | −25.9253 | 29.23846 | 94.46029 |
| −6.431364 | −7.03772 | 17.46511 | 8.593303 | −11.2606 | −15.2183 | −22.7106 | 88.0059 |
| −6.908485 | 0.252328 | −26.289 | −16.2536 | −38.3508 | 24.06692 | 0.862923 | 74.79468 |
| −7.385606 | −7.9042 | 9.754791 | −36.828 | −37.3765 | 18.66184 | 30.04996 | 16.30664 |
| −7.862728 | −25.3779 | −25.5195 | −24.1306 | −27.7846 | 12.04921 | −9.82414 | 15.3532 |
| −8.339849 | 10.94666 | −18.4292 | −40.1562 | −31.861 | 22.59342 | −1.72845 | −9.20905 |
| −8.81697 | −3.84146 | −1.60828 | 16.50199 | −39.1634 | −28.8935 | −40.0203 | −3.66343 |

TABLE 3-continued

| | | | | | | | |
|---|---|---|---|---|---|---|---|
| −9.294091 | −8.84657 | −15.2446 | −18.5536 | 7.386567 | 25.68153 | −17.1855 | −1.83995 |
| −9.771213 | −4.61808 | −34.3714 | 18.07751 | −20.3263 | −18.7347 | 11.37383 | 6.132259 |

| Concentration | C9 | | | C10 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 4.489008 | 5.780424 | −12.3845 | 32.72604 | −1.3151 | 6.509968 | 100.8895 |
| −5.477121 | 11.7879 | −28.9568 | 40.0395 | −40.5518 | −33.9801 | −29.38 | 98.1315 |
| −5.954243 | −27.4365 | −18.8961 | −2.50749 | 1.691881 | 1.059233 | 6.714616 | 94.46029 |
| −6.431364 | −0.31304 | −39.3941 | 8.568971 | 5.142818 | 22.78571 | 17.93225 | 88.0059 |
| −6.908485 | −5.30467 | 29.2878 | 1.821058 | −33.073 | −31.3707 | −29.8413 | 74.79468 |
| −7.385606 | 3.734113 | −2.05009 | −2.9843 | −10.1816 | −6.75334 | 26.24217 | 16.30664 |
| −7.862728 | −39.2155 | −18.1272 | −20.2487 | 15.12705 | −1.73848 | 6.046685 | 15.3532 |
| −8.339849 | −0.12562 | −13.9689 | −7.52782 | 8.978043 | −22.8617 | −7.75883 | −9.20905 |
| −8.81697 | 8.520622 | 5.537094 | 14.33727 | −2.4201 | −9.22566 | −27.2736 | −3.66343 |
| −9.294091 | −8.9486 | 1.419335 | −17.5352 | 1.539957 | 4.023809 | −27.1512 | −1.83995 |
| −9.771213 | 11.24507 | 24.89889 | −7.66726 | 37.53523 | −6.39515 | −0.95943 | 6.132259 |

| Concentration | C11 | | | C12 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 21.45849 | 27.00526 | 27.99146 | 4.799508 | 9.81866 | 33.12021 | 100.4281 |
| −5.477121 | −31.6507 | 7.262713 | −22.9178 | 17.07896 | 10.71564 | −24.3861 | 98.6132 |
| −5.954243 | −4.23774 | −36.7341 | 20.91248 | −6.27828 | −0.39781 | −34.2094 | 98.05019 |
| −6.431364 | −5.12705 | 20.93564 | 1.209367 | −19.6532 | 18.26483 | 23.78456 | 93.04975 |
| −6.908485 | −2.04142 | 19.82091 | −11.6525 | −12.7604 | −44.4926 | −26.034 | 89.45811 |
| −7.385606 | 23.70626 | 17.97183 | 5.904263 | 34.20857 | 34.3645 | −6.3512 | 47.8261 |
| −7.862728 | 6.249828 | −9.98796 | 0.828934 | −15.5049 | −21.1087 | −35.3885 | 28.98286 |
| −8.339849 | 11.37375 | 16.24813 | 12.51833 | −22.9805 | −5.84707 | −6.17003 | 3.941144 |
| −8.81697 | −7.93664 | −6.3406 | 10.11275 | 12.37748 | −1.73804 | 20.01369 | −8.05055 |
| −9.294091 | −26.4146 | −18.261 | −33.6664 | 3.022523 | −13.8837 | 0.217719 | −3.76273 |
| −9.771213 | −20.9598 | 11.81976 | −13.6145 | 18.0501 | −20.103 | −38.0781 | −1.911 |

| Concentration | C13 | | | C14 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 98.36784 | 95.2799 | 96.14817 | 103.2945 | 102.1097 | 103.2736 | 100.4281 |
| −5.477121 | 87.84198 | 83.27731 | 83.50867 | 106.1285 | 105.9119 | 107.3553 | 98.6132 |
| −5.954243 | 75.44346 | 83.23603 | 79.30265 | 84.31701 | 92.47757 | 91.04928 | 98.05019 |
| −6.431364 | 54.65901 | 24.56393 | 41.98704 | 40.16475 | 62.73851 | 47.64906 | 93.04975 |
| −6.908485 | −13.6386 | 2.206529 | −0.67812 | 42.6475 | 14.48349 | 29.53025 | 89.45811 |
| −7.385606 | 35.8205 | 18.90853 | 45.6947 | 5.293268 | 31.48621 | 31.78721 | 47.8261 |
| −7.862728 | 7.61974 | −2.13549 | −0.78096 | −24.902 | 51.04536 | 18.00119 | 28.98286 |
| −8.339849 | 30.02611 | 27.22016 | 3.938939 | 33.24314 | −0.7378 | 10.67377 | 3.941144 |
| −8.81697 | −22.4972 | 19.34481 | 15.31759 | −19.9622 | 10.71795 | 11.92987 | −8.05055 |
| −9.294091 | 4.979932 | −28.5437 | 23.09991 | 15.16754 | 29.87882 | 11.08606 | −3.76273 |
| −9.771213 | 3.18964 | −35.8803 | −3.23056 | −4.69973 | 3.389463 | −14.8291 | −1.911 |

| Concentration | C15 | | | C16 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 2.450829 | 0.025709 | 3.528513 | 9.049217 | 12.23356 | −4.64098 | 100.4281 |
| −5.477121 | −27.0586 | 9.931496 | 22.98634 | −39.9404 | 6.381835 | −17.9195 | 98.6132 |
| −5.954243 | 7.391346 | −32.1137 | −21.9369 | −11.9388 | 15.0488 | −17.1213 | 98.05019 |
| −6.431364 | −27.031 | −17.0364 | −35.2534 | −10.0734 | 23.95272 | 14.02808 | 93.04975 |
| −6.908485 | −19.189 | −13.1875 | −18.6652 | −5.22099 | −7.47664 | −6.35807 | 89.45811 |
| −7.385606 | −1.53526 | −25.3583 | −1.38134 | −34.3838 | −5.34739 | −17.0011 | 47.8261 |
| −7.862728 | 3.911324 | 12.70592 | 11.15824 | 29.49345 | −35.6517 | −4.33241 | 28.98286 |
| −8.339849 | −1.82505 | −0.32445 | 22.70625 | 0.113784 | −22.168 | 2.692058 | 3.941144 |
| −8.81697 | 8.351451 | 1.505195 | 30.16285 | −7.7562 | −6.83617 | −15.6271 | −8.05055 |
| −9.294091 | −22.3536 | −0.35562 | 18.35494 | −18.7476 | −0.88687 | −4.2237 | −3.76273 |
| −9.771213 | −29.5339 | −3.45996 | 2.160174 | −11.5867 | −27.0158 | −2.25023 | −1.911 |

| Concentration | C17 | | | C18 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 7.814834 | −18.7271 | −39.712 | 20.41717 | −21.9235 | 39.73831 | 100.4281 |
| −5.477121 | −21.4793 | 21.66169 | −34.5604 | −47.4694 | −7.05033 | −26.1305 | 98.6132 |
| −5.954243 | −43.3089 | 0.113663 | −18.0925 | −6.59348 | −12.6979 | −7.93561 | 98.05019 |
| −6.431364 | −23.0497 | −5.46763 | −15.6262 | −17.6346 | −19.0398 | −30.7091 | 93.04975 |

TABLE 3-continued

| | | | | | | | |
|---|---|---|---|---|---|---|---|
| −6.908485 | −24.7454 | −43.349 | −22.0993 | −1.7783 | 1.234805 | −33.0095 | 89.45811 |
| −7.385606 | 7.80625 | −39.1892 | −15.7379 | −23.0256 | −11.8751 | 28.0322 | 47.8261 |
| −7.862728 | −7.46562 | −68.4482 | −20.2046 | 12.90464 | −9.84093 | −11.508 | 28.98286 |
| −8.339849 | −22.1581 | 13.25272 | −27.493 | −32.3776 | 1.360505 | −14.8079 | 3.941144 |
| −8.81697 | 10.6136 | 2.858905 | −44.4852 | 32.81712 | 28.79609 | −38.9051 | −8.05055 |
| −9.294091 | 3.42252 | 8.940037 | −51.9949 | 9.372862 | −12.2856 | −13.1795 | −3.76273 |
| −9.771213 | 1.878418 | 11.84952 | −9.81694 | −5.78329 | −6.94506 | 15.9268 | −1.911 |
| Concentration | C19 | | | C20 | | | L-168,049 |
| gradient LogM | Inhibition percentage | Inhibition percentage | Inhibition percentage | Inhibition percentage | Inhibition percentage | Inhibition percentage | Inhibition percentage |
| −5 | 34.07259 | −35.2218 | −6.71092 | 18.1581 | −39.4147 | 2.043708 | 100.4281 |
| −5.477121 | 11.30968 | 29.49002 | 31.79587 | −16.9934 | 2.365699 | −3.05239 | 98.6132 |
| −5.954243 | 10.99531 | 5.631229 | 41.03634 | 12.90692 | −13.0114 | −8.73296 | 98.05019 |
| −6.431364 | 18.95094 | 10.74806 | −13.2223 | 7.253805 | −8.40831 | 5.904631 | 93.04975 |
| −6.908485 | −25.5981 | 0.985976 | 0.434258 | 24.47322 | 14.07576 | 33.94305 | 89.45811 |
| −7.385606 | −1.71538 | 24.36076 | −4.49796 | −9.86884 | 2.657783 | 34.57254 | 47.8261 |
| −7.862728 | 6.139602 | 14.66942 | −12.5289 | −8.83545 | 12.40652 | −24.3369 | 28.98286 |
| −8.339849 | −35.1624 | −10.5336 | −2.96128 | 3.4469 | −8.56771 | −5.41089 | 3.941144 |
| −8.81697 | 31.1282 | −1.14472 | −11.2501 | 14.95257 | 16.5898 | 44.82866 | −8.05055 |
| −9.294091 | 10.09647 | 28.37046 | 17.52129 | −40.3815 | 9.302105 | 9.666315 | −3.76273 |
| −9.771213 | −6.75399 | −19.8704 | 11.16038 | −1.23546 | 5.313066 | 21.17244 | −1.911 |
| Concentration | C21 | | | C22 | | | L-168,049 |
| gradient LogM | Inhibition percentage | Inhibition percentage | Inhibition percentage | Inhibition percentage | Inhibition percentage | Inhibition percentage | Inhibition percentage |
| −5 | −42.7197 | −40.82 | −6.17334 | −30.5862 | 16.50023 | −1.00033 | 100.5604 |
| −5.477121 | −53.9423 | −47.186 | −21.3641 | −57.5005 | −12.8689 | −34.1965 | 96.62153 |
| −5.954243 | 21.78096 | −1.82111 | 3.319337 | −11.4422 | 17.90716 | −23.1384 | 95.17342 |
| −6.431364 | 27.77292 | −18.0508 | 9.924084 | −65.059200* | −9.83757 | −38.5336 | 91.89666 |
| −6.908485 | −55.969900* | −67.355300* | −14.3303 | −59.258300* | −48.0506 | −31.7455 | 78.16119 |
| −7.385606 | −38.8149 | −0.62746 | −54.5274 | −5.73492 | 1.577532 | −3.87531 | 46.68825 |
| −7.862728 | −19.5624 | 26.74542 | −38.8977 | −41.331 | −24.4309 | 23.83835 | 33.52469 |
| −8.339849 | −16.4657 | −37.8127 | 25.10431 | −3.2511 | 21.51812 | −22.2925 | −19.5336 |
| −8.81697 | −28.5528 | 13.99508 | −19.2725 | −1.04743 | −27.6336 | −52.9651 | 22.63393 |
| −9.294091 | 33.24786 | −16.9023 | 17.91219 | −5.112 | 10.46791 | −17.7298 | 19.0859 |
| −9.771213 | −49.0707 | −18.6164 | −5.68068 | −34.2012 | 3.477508 | −5.28374 | 1.646174 |
| Concentration | C23 | | | C24 | | | L-168,049 |
| gradient LogM | Inhibition percentage | Inhibition percentage | Inhibition percentage | Inhibition percentage | Inhibition percentage | Inhibition percentage | Inhibition percentage |
| −5 | 75.66265 | 75.13544 | 57.57891 | −10.9856 | 2.297213 | −15.1187 | 100.5604 |
| −5.477121 | 20.07258 | 43.03023 | 5.134522 | −6.38747 | −23.2283 | 7.8078 | 96.62153 |
| −5.954243 | −0.8394 | 41.49496 | 8.766312 | −12.0514 | 0.761549 | 1.112782 | 95.17342 |
| −6.431364 | −15.2381 | −9.68248 | 6.049052 | −49.0215 | −15.3222 | −46.9302 | 91.89666 |
| −6.908485 | 4.280152 | 12.02751 | −71.091500* | −52.9455 | −56.6235 | −5.83182 | 78.16119 |
| −7.385606 | −31.8529 | 12.3235 | −11.7931 | −6.07678 | −5.63608 | −26.4358 | 46.68825 |
| −7.862728 | −76.091900* | −26.5916 | −31.2095 | −5.35373 | −21.4306 | −33.6957 | 33.52469 |
| −8.339849 | −15.8448 | 23.02911 | −17.3448 | −42.5342 | −2.30491 | −36.5898 | −19.5336 |
| −8.81697 | −28.8951 | 17.21836 | 14.27307 | −23.6956 | 17.50362 | −36.9708 | 22.63393 |
| −9.294091 | 7.800055 | 24.08749 | −12.9822 | −16.2822 | 0.171539 | −55.6223 | 19.0859 |
| −9.771213 | −42.3231 | 44.27058 | −2.62025 | −66.6615 | −3.7793 | −50.5947 | 1.646174 |
| Concentration | C25 | | | C26 | | | L-168,049 |
| gradient LogM | Inhibition percentage | Inhibition percentage | Inhibition percentage | Inhibition percentage | Inhibition percentage | Inhibition percentage | Inhibition percentage |
| −5 | 8.161618 | −0.73687 | 49.3189 | 16.60552 | −26.5175 | −5.9826 | 100.5604 |
| −5.477121 | −14.9937 | −20.5786 | 7.536136 | −27.6759 | −0.86548 | −35.8233 | 96.62153 |
| −5.954243 | −31.4725 | 1.59208 | −42.8834 | −39.1019 | −16.9961 | −11.7971 | 95.17342 |
| −6.431364 | 27.05132 | 7.403896 | 41.96233 | −26.4461 | −52.8129 | −39.6412 | 91.89666 |
| −6.908485 | −43.5173 | −14.2199 | −76.6858 | −25.9687 | −12.3017 | −11.3498 | 78.16119 |
| −7.385606 | −24.7275 | −36.5786 | 13.76706 | −38.8293 | −45.2629 | 0.210664 | 46.68825 |
| −7.862728 | 17.73872 | 36.43395 | 29.72938 | −14.0435 | −42.9647 | −5.60207 | 33.52469 |
| −8.339849 | −22.3882 | −39.6366 | −40.6625 | 5.791446 | −19.5966 | 9.198763 | −19.5336 |
| −8.81697 | −32.0254 | −37.1231 | −52.6473 | −9.84122 | −10.6246 | −47.3524 | 22.63393 |
| −9.294091 | −56.6628 | −19.4824 | 10.50452 | −0.1124 | 9.630004 | 28.05575 | 19.0859 |
| −9.771213 | −140.839 | −8.89688 | 17.2997 | −17.8823 | 2.340118 | 20.41762 | 1.646174 |

TABLE 3-continued

| Concentration | C27 | | | C28 | | | L-168,049 |
|---|---|---|---|---|---|---|---|
| gradient LogM | Inhibition percentage | Inhibition percentage | Inhibition percentage | Inhibition percentage | Inhibition percentage | Inhibition percentage | Inhibition percentage |
| −5 | 17.73558 | −48.9678 | 36.75353 | 31.40869 | −54.3544 | −60.6171 | 100.5604 |
| −5.477121 | −13.4598 | −78.7253 | 6.21246 | 14.39916 | 19.28817 | −55.5558 | 96.62153 |
| −5.954243 | −68.7512 | −13.923 | −68.5079 | −24.2875 | 38.00314 | −25.343 | 95.17342 |
| −6.431364 | −29.4768 | −45.8369 | −48.8129 | 34.36428 | −1.71369 | −37.8756 | 91.89666 |
| −6.908485 | −2.49091 | −20.0347 | −51.5915 | −43.4925 | 5.619733 | 2.448334 | 78.16119 |
| −7.385606 | −12.2442 | 25.23883 | −48.6066 | −21.3641 | −7.80414 | −1.89249 | 46.68825 |
| −7.862728 | −12.8566 | −60.2134 | 1.10327 | 14.56813 | 25.73587 | −8.62761 | 33.52469 |
| −8.339849 | −24.7315 | −29.8299 | −20.459 | −6.70335 | −16.2867 | −3.68355 | −19.5336 |
| −8.81697 | −19.8783 | 20.75261 | −6.84695 | −27.3759 | 21.56875 | 34.83851 | 22.63393 |
| −9.294091 | −30.7083 | −13.4815 | −50.8699 | −50.8468 | 11.9284 | −1.61008 | 19.0859 |
| −9.771213 | −13.3454 | −44.3837 | −24.0621 | −21.813 | −45.1414 | 6.246463 | 1.646174 |
| Concentration | C29 | | | C30 | | | L-168,049 |
| gradient LogM | Inhibition percentage | Inhibition percentage | Inhibition percentage | Inhibition percentage | Inhibition percentage | Inhibition percentage | Inhibition percentage |
| −5 | 21.38173 | −23.7881 | 30.57214 | −31.6544 | −30.6279 | 24.26864 | 100.5604 |
| −5.477121 | 45.01686 | 12.5193 | 22.19625 | −6.69537 | −22.7315 | −38.7442 | 96.62153 |
| −5.954243 | 45.8205 | 2.137398 | 5.001465 | 10.08965 | −15.8104 | −4.7884 | 95.17342 |
| −6.431364 | −18.994 | −12.4118 | −48.7182 | 13.3859 | −77.9226 | 18.45847 | 91.89666 |
| −6.908485 | −12.9208 | 1.518078 | −12.6029 | 21.79603 | −50.2766 | 9.098346 | 78.16119 |
| −7.385606 | −8.36925 | 3.923759 | 16.36132 | −77.3092 | −39.7196 | −16.5711 | 46.68825 |
| −7.862728 | −10.6825 | −9.79216 | −61.623 | 2.209033 | −48.0745 | 19.49895 | 33.52469 |
| −8.339849 | −61.2695 | −33.3603 | −64.963 | −11.1792 | −39.2013 | −24.2246 | −19.5336 |
| −8.81697 | −26.212 | −34.661 | 4.968303 | −6.91135 | −15.7719 | −47.0794 | 22.63393 |
| −9.294091 | −12.0267 | 1.83427 | −62.0128 | −7.167 | 41.78717 | −53.1934 | 19.0859 |
| −9.771213 | −29.6773 | 7.587787 | −31.3932 | −48.4113 | −5.63768 | 16.31158 | 1.646174 |

Figure 14:
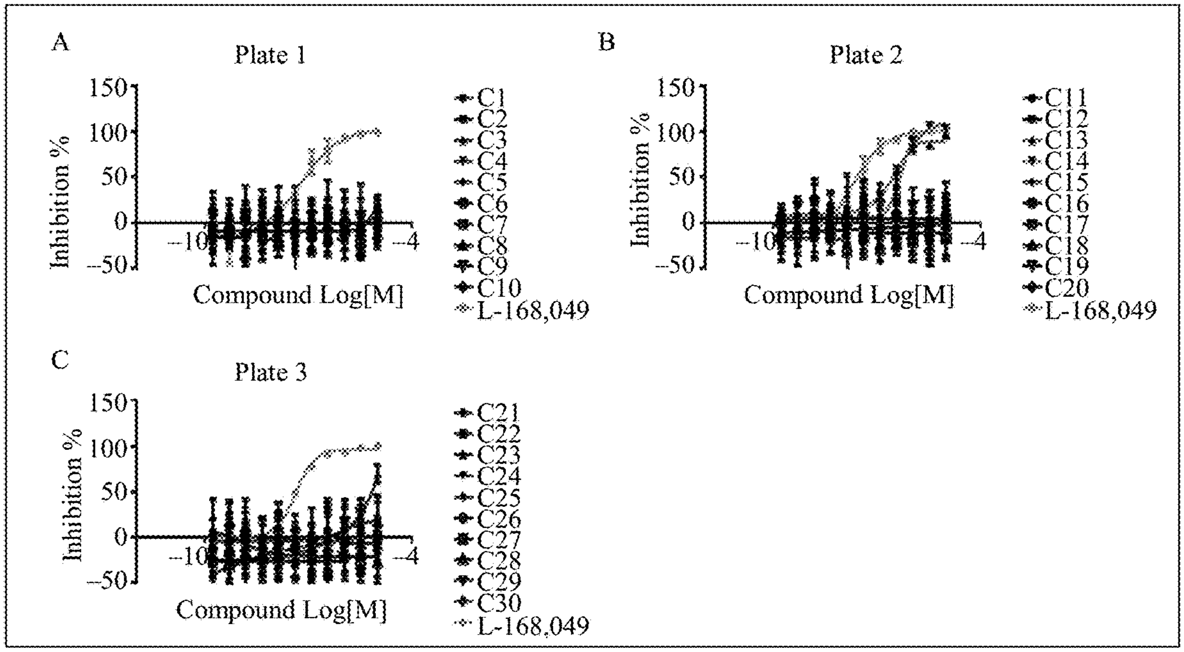
FIG. 14 is a curve graph showing the experimental results of the response of 30 compounds (where A corresponds to C1-C10, B corresponds to C11-C20, and C corresponds to C21-C30, with L-168,049 as a positive control) in Table 2 to cAMP.

The data in Table 3 is processed through software using the concentration gradient as the abscissa and the inhibition percentage as the ordinate, to obtain FIG. 14 and Table 4. This figure shows the inhibition percentages of the responses of L-168,049 and 30 target drug small molecules respectively. L-168,049 is a positive control. It can be learned from this figure that both C13 and C14 have the activity, while the remaining 28 target drug small molecules show no activity value.

TABLE 4

| Number | IC50(M) |
|---|---|
| C1 | >10E−05 |
| C2 | >10E−05 |
| C3 | >10E−05 |
| C4 | >10E−05 |
| C5 | >10E−05 |
| C6 | >10E−05 |
| C7 | >10E−05 |
| C8 | >10E−05 |
| C9 | >10E−05 |
| C10 | >10E−05 |
| L-168,049 | 6.146E−08 |
| C11 | >10E−05 |
| C12 | >10E−05 |
| C13 | 4.465E−07 |
| C14 | 4.225E−07 |
| C15 | >10E−05 |
| C16 | >10E−05 |
| C17 | >10E−05 |
| C18 | >10E−05 |
| C19 | >10E−05 |
| C20 | >10E−05 |
| L-168,049 | 2.082E−08 |
| C21 | >10E−05 |
| C22 | >10E−05 |
| C23 | >10E−05 |
| C24 | >10E−05 |
| C25 | >10E−05 |

TABLE 4-continued

| Number | IC50(M) |
|---|---|
| C26 | >10E−05 |
| C27 | >10E−05 |
| C28 | >10E−05 |
| C29 | >10E−05 |
| C30 | >10E−05 |
| L-168,049 | 4.215E−08 |

Table 4 shows the half maximal inhibitory concentration IC50 of 30 tested target drug small molecules. For example, the values of half maximal inhibitory concentration IC50 of compound C13 and compound C14 are small, which are 446.5 nM and 422.5 nM respectively, so they can be used as structurally novel human glucagon receptor antagonists.

This technical solution combines the advantages of deep learning and virtual screening. The simulated drug molecule is obtained through prediction based on a deep learning model, to increase the diversity of the chemical space structure of the simulated drug molecule, so that the skeleton structure of the antagonist determined according to the simulated drug molecule is quite different from the skeleton structure of the existing drug, which is beneficial to improving the diversity of drugs. In addition, the small molecule database to be screened is determined according to the simulated drug molecule, and virtual screening is performed on the small molecule database according to the target receptor molecule, so that the target drug small molecule can directly search for a proper conformation in the protein active pocket of the target receptor, which is beneficial to ensuring the appropriateness of the designed antagonist. It can be seen that this technical solution can reduce the cost and time of drug research and development and is beneficial to improving the diversity of drugs.

Other embodiments of the present disclosure will be apparent to a person skilled in the art from consideration of the specification and practice of the disclosure here. The present disclosure is intended to cover any variation, use, or adaptive change of the present disclosure. These variations, uses, or adaptive changes follow the general principles of the present disclosure and include common general knowledge or common technical means in the art that are not disclosed in the present disclosure. The specification and the embodiments are considered as merely exemplary, and the scope and spirit of the present disclosure are pointed out in the following claims.

It is to be understood that the present disclosure is not limited to the precise structures described above and shown in the accompanying drawings, and various modifications and changes can be made without departing from the scope of the present disclosure.

What is claimed is:

1. A compound represented by the following structural formula A, or a stereoisomer , pharmaceutically acceptable ester, or pharmaceutically acceptable salt thereof, (A)

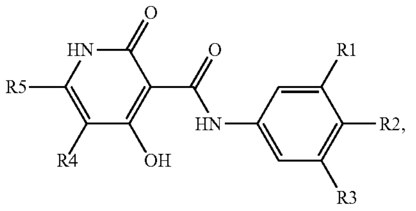

wherein R1 is H, F, Cl, Br, or I;

R2 is H or —O—$(CH_2)_m$—$CH_3$, m being an integer of 0-2;

R3 is H or —S—$(CH_2)_n$—$CH_3$, n being an integer of 0-2; and

R4 and R5 together form

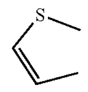
or
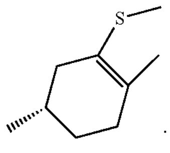
.

wherein the point of attachment for the sulfur atom is at the R5 position.

2. The compound according to claim 1, wherein in the structural formula A, R1 is —Cl.

3. The compound according to claim 1, wherein in the structural formula A, R2 is —O—$CH_3$.

4. The compound according to claim 1, wherein in the structural formula A, R3 is —S—$CH_3$.

5. The compound according to claim 1, wherein the compound is a compound A1 represented by the following structural formula A1:

(A1)

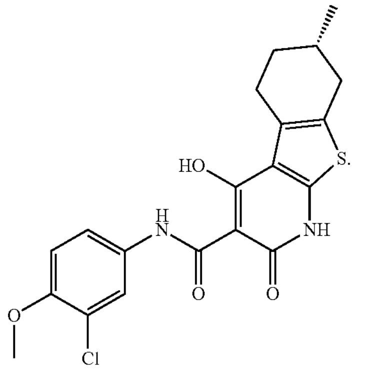

6. The compound according to claim 1, wherein the compound is a compound A2 represented by the following structural formula A2:

(A2)

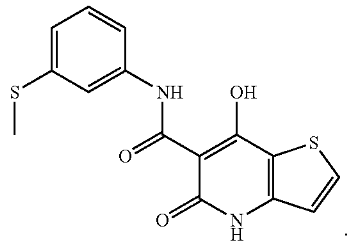
.

7. A pharmaceutical composition, comprising a pharmaceutically acceptable carrier and the compound according to claim 1.

8. The pharmaceutical composition according to claim 7, wherein the pharmaceutical composition is a solution, a tablet, or a capsule.

9. The pharmaceutical composition according to claim 8, wherein the pharmaceutical composition is administered by injection or orally.

10. A method for preparing a pharmaceutical composition for use as a glucagon receptor antagonist, the pharmaceutical composition comprising a pharmaceutically acceptable carrier and the compound represented by the following structural formula A, or a stereoisomer, pharmaceutically acceptable ester, or pharmaceutically acceptable salt thereof, (A)

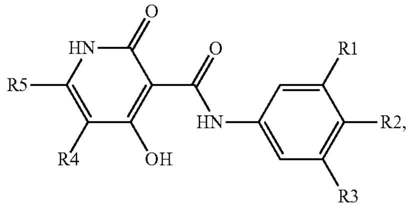

wherein R1 is H, F, Cl, Br, or I;

R2 is H or $—O—(CH_2)_m—CH_3$, m being an integer of 0-2;

R3 is H or $—S—(CH_2)_n—CH_3$, n being an integer of 0-2; and

R4 and R5 together form

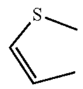
or
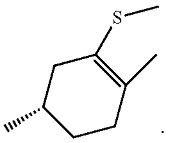
.

11. The method according to claim 10, wherein the drug is used for treatment of at least one of diabetes, disorders of glucagon levels, or hyperglycemia.

12. The method according to claim 10, wherein the drug is used for mammals.

13. The method according to claim 12, wherein the drugs are used for human.

14. A method for antagonizing human glucagon receptor (hGCGR), comprising administering an effective dose of a compound represented by the following structural formula A or a stereoisomer, pharmaceutically acceptable ester, or pharmaceutically acceptable salt thereof, or a pharmaceutical composition comprising a pharmaceutically acceptable carrier and a compound represented by the following structural formula A or a stereoisomer, pharmaceutically acceptable ester, or pharmaceutically acceptable salt thereof, (A)

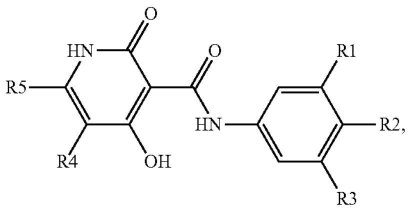

wherein R1 is H, F, Cl, Br, or I;

R2 is H or $—O—(CH_2)_m—CH_3$, m being an integer of 0-2;

R3 is H or $—S—(CH_2)_n—CH_3$, n being an integer of 0-2; and

R4 and R5 together form

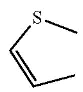
or
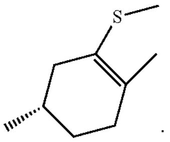
.

wherein the point of attachment for the sulfur atom is at the R5 position.

15. The method according to claim 14, wherein in the structural formula A, R1 is —Cl.

16. The method according to claim 14, wherein in the structural formula A, R2 is $—O—CH_3$.

17. The method according to claim 14, wherein in the structural formula A, R3 is $—S—CH_3$.

18. The method according to claim 14, wherein the compound is a compound A1 represented by the following structural formula A1:

(A1)

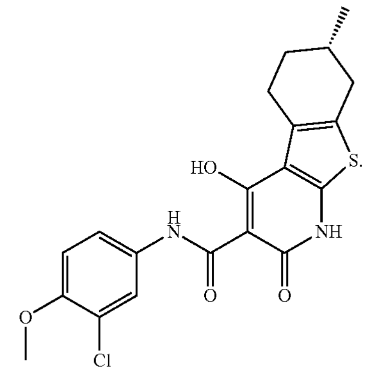

19. The method according to claim 14, wherein the compound is a compound A2 represented by the following structural formula A2:

(A2)

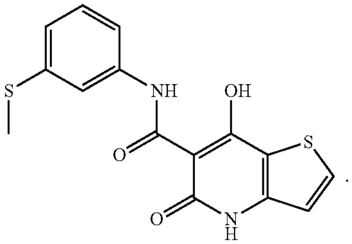

20. The method according to claim 14, wherein the pharmaceutical composition is a solution, a tablet, or a capsule.

* * * * *